United States Patent [19]

Wilson et al.

[11] Patent Number: 5,798,239
[45] Date of Patent: Aug. 25, 1998

[54] GLYCOSYLATION VARIANTS OF IDURONATE 2-SULFATASE

[75] Inventors: Peter J. Wilson, North Adelaide; Charles Phillip Morris, Plympton; Donald Stewart Anson, Thebarton; Teresa Occhiodoro, Prospect; Julie Bielicki, Burnside; Peter Roy Clements, West Lakes; John Joseph Hopwood, Stonyfell, all of Australia

[73] Assignee: Women's and Children's Hospital, North Adelaide, Australia

[21] Appl. No.: 484,494

[22] Filed: Jun. 7, 1995

Related U.S. Application Data

[62] Division of Ser. No. 345,212, Nov. 28, 1994, which is a continuation of Ser. No. 991,973, Dec. 17, 1992, which is a continuation-in-part of Ser. No. 790,362, Nov. 12, 1991, abandoned.

[51] Int. Cl.$^6$ .......................... A61K 38/46; A61K 38/47; C12N 9/00
[52] U.S. Cl. .................. 435/183; 424/94.6; 424/94.61; 435/183
[58] Field of Search ................... 435/183; 424/94.6, 424/94.61

[56] References Cited

U.S. PATENT DOCUMENTS 4,866,042  9/1989  Neuwelt .................................. 424/93.2

OTHER PUBLICATIONS

Wilson, et al. (1990) Hunter Syndrome: Isolation of an Iduronate-2-Sulfatase cDNA and Analysis of Patient DNA. Proc. Natl. Acad. Sci. USA 87:8531–8535.

Neufeld, et al. (1989) in The Metabolic Basis of Inherited Disease, entitled "The Mucopolysaccharidoses", eds Scriver, CR. Beauden, AL, Sly, WS & Valle, D (McGraw-Hill), New York pp. 1565–1587.

Shapiro, (1989) in The Metabolic Basis of Inherited Disease, entitled "Steroid Sulfatase Deficiency and Z-linked Ichthyosis,", eds Scriver, CR, Beauden, AL, Sly, WS & Valle, D (McGraw-Hill, New York) pp. 1945–1964.

Bielicki, et al. (1990) "Human liver iduronate-2-sulphatase" Biochem J 271: pp. 75–86.

Nelson, et al. (1989) "Cystic fibrosis:prenatal diagnosis and carrier detection by DNA analysis" Med J Aust 151:pp. 126–131.

Stein, et al. (1989) "Cloning and Expression of Human Arylsulfatase A*", J Biol Chem 264(2):pp. 1252–1259.

Peters, et al. (1990) "Phylogenetic Conservation of Arylsulfatases" J Biol Chem 265(6):pp. 3374–3381.

Yen, et al. (1988) "The Human X-Linked Steroid Sulfatase Gene and a Y-Encoded Pseudogene:Evidence for an Inversion of the Y Chromosome during Primate Evolution" Cell 55:pp. 1123–1135.

Robertson, et al. (1988) "Human Glucosamine-6-sulfatase cDNA Reveals Homology with Steroid Sulfatase" Biochem Biophys Res Commun 157(1) pp.: 218–224.

Yen, et al. (1987) "Cloning and Expression of Steroid Sulfatase cDNA and the Frequent Occurrence of Deletions in STS Deficiency:Implications for X–Y Interchange" Cell 49:pp. 443–454.

Stein, et al. (1989) "Cloning and Expression of Human Steroid–sulfatase" J Biol Chem 264(23):pp. 13865–13872.

Sasaki, et al. (1988) "cDNA cloning, nucleotide sequence and expression of the gene for arylsulfatase in the sea urchin (*Hemicentrotus pulcherrimus*) embryo" Eur J Biochem 177:pp. 9–13.

Anson, et al. (1992) "Correction of human mucopolysaccharidosis type VI fibroblasts with recombinant N-acetylgalactosamine-4-sulphatase" Biochem J 284:pp. 289–794.

Bielicki et al. (1993) "Recombinant Human Iduronate-2-Sulphatse: Correction of Mucopolysacchoridosis-Type II Fibtroblasts and Characterization of the Purific Enzyme" Biochem. J. 289: 241–246.

Gottesman, (1987) "Chinese Hamster Ovary Cells" Meth. Enzymol. 157: 3–8.

American Type Culture Collector Catalog of Cell Lines and Hybridomas, Seventh Edition, 1992, p. 166.

Darnell et al. (1986) in Molecular Cell Biology, entitled "Protein Glycosylation" (Scientific American Books, New York, New York) pp. 957–964.

Ferrara et al., (1987) "Characterization of Recombinant Glycosylated Human Interleutin-2 Produced by a Recombinant Plasma Transformed CHO Cell Line" Febs. Lett. 266(1): 47–52.

Kodama et al., (1992) "Characterization of Recombinant Murie Interleution 5 Express in Chinese HAmster Ovary Cells" Glycobiol. 2(5): 419–427.

Ratner, M. (1989) Protein Expression in Yeast, Biotechnology 7: 1129–1133, Nov. 1989.

Hay, R. et al. (Eds), (1988) American Type Culture Collector Catalog of Cell Lines and Hybridomas, Sixth Ed. 1988, p. 169.

*Primary Examiner*—Robert A. Wax
*Assistant Examiner*—Einar Stole
*Attorney, Agent, or Firm*—Scully, Scott, Murphy & Presser

[57] ABSTRACT

The present invention provides a highly glycosylated iduronate-2-sulfatase enzyme comprising an iduronate-2-sulfatase polypeptide with at least 5 kilodalton (kDa) more sugar than iduronate-2-sulfatase purified from a natural source, e.g. human liver. The present invention also provides an enzymatically active polypeptide fragment or variant of such a highly glycosylated iduronate-2-sulfatase. The present invention further provides an isolated nucleic acid encoding iduronate-2-sulfatase, as well as an expression vector, a host cell and a method for producing the present highly glycosylated iduronate-2-sulfatase enzyme. In one embodiment the present invention is directed to a method for producing a glycosylated iduronate-2-sulfatase enzyme which comprises culturing a host cell containing a nucleic acid encoding an enzymatically active iduronate-2-sulfatase polypeptide wherein the host cell glycosylates the polypeptide to a greater degree than a native iduronate-2-sulfatase polypeptide expressed by a natural human liver cell.

5 Claims, 25 Drawing Sheets

```
CGGCTGTGTTGCGCAGTCTTCATGGTTCCCGACGAGGAGTCTCTGTGGCTGGGGC                              60

TGCTAACTGCGCCACCTGCTGCAGCCTGTCCCCGCGCTCTGAAGCGCCGCTCGAAGC                            120
                                    M  P  P  P  R  T  G  R  G  L  L  W  L  G  L  V  L  S    19

CGAAATGCCGCCCCCGGACCGGCCGAGGCCTTCTGGCTGGGTTCTGAGCTC                                  180
                              *
 V  C  V  A↓L  G↓S  E  T  Q  A  N  S  T  D  A  L  N  V                              39

CGTCTGCGTCGCCCTCGGATCCGAAACGCAGCCAACTCGACCACAGATGCTCTGAACGT                          240
                                                           L  L  I  V  D  D  L  R  P  S  L  G  C  Y  G  D  K  L  V    59

CTGCTGATCGTGGATGACCTGCGCCCCTCCCTGGGCTGTTATGGGGATAAGCTGGT                             320

TCTTCTCATCATCGGT
```

FIGURE 1-1

```
    R   S   P   N   I   D   Q   L   A   S   H   S   L   L   F   Q   N   A   F   A    79
    GAGGTCCCCAAATATTGACCAACTGGCATCCCACAGCCTCCTCTTCCAGAATGCCTTTGC                     360

Q   Q   A   V   C   A   P   S   R   V   S   F   L   T   G   R   R   P   D   T    99
    GCAGCAAGCAGTGTGCGCCCCGAGCCGCGTTTCTTCCTCACTGGCAGGAGACCTGACAC                     420

*
    T   R   L   Y   D   F   N   S   Y   W   R   V   H   A   G   N   F   S   T   I   119
    CACCCGCCTGTACGACTTCAACTCCTACTGGAGGGTGCACGCTGGAAACTTCTCCACCAT                     480

P   Q   Y   F   K   E   N   G   Y   V   T   M   S   V   G   K   V   F   H   P   139
    CCCCCAGTACTTCAAGGAGAATGGCTATGTGACCATGTCGGTGGGAAAAGTCTTTCACCC                     540
```

FIGURE 1-2

```
     *
     G   I   S   S   N   H   T   D   D   S   P   Y   S   W   S   F   P   P   Y   H    159
     TGGGATATCTTCTAACCATACCGATGATTCTCCGTATAGCTGGTCTTTTCCACCTTATCA                      600

P   S   S   E   K   Y   E   N   T   K   T   C   R   G   P   D   G   E   L   H    179
     TCCTTCCTCTGAGAAGTATGAAAACACTAAGACATGTCGAGGGCCAGATGGAGAACTCCA                      660

A   W   L   L   C   P   V   D   V   L   D   V   P   E   G   T   L   P   D   K    199
     TGCCAACCTGCTTTGCCCCGTGGATGTGCTGGATGTTCCCGAGGGCACCTTGCCTGACAA                      720

Q   S   T   E   Q   A   I   Q   L   L   E   K   M   K   T   S   A   S   P   F    219
     ACAGAGCACTGAGCAAGCCATACAGTTGTTGGAAAAGATGAAAACGTCAGCCAGTCCTTT                      780
```

FIGURE 1-3

```
F L A V G Y H K P H I P F R Y P K E F Q          239
CTTCCTGGCCGTTGGGTATCATAAGCCACACATCCCCTTCAGATACCCAAGGAATTTCA    840
                        *
K L Y P L E N I T L A P D D P E V P D G L        259
GAAGTTGTATCCCTTGGAGAACATCACCCTGGCCCCCGATCCCGAGTTCCCTGATGGCCT   900

P P V A Y N P W M D I R Q R E D V Q A L          279
ACCCCCTGTGGCCTACAACCCCTGGATGGACATCAGGCAACGGGAAGACGTCCAAGCCTT   960
        *
N I S V P Y G P I P V D F Q R K I R Q S          299
AAACATCAGTGTGCCGTATGGTCCAATTCCTGTGGACTTTCAGCGGAAAAATCCGCCAGAG 1020
```

FIGURE 1-4

```
Y  F  A  S  V  S  Y  L  D  T  Q  V  G  R  L  L  S  A  L  D    319
CTACTTTGCCTCTGTCATATTTGGATACACAGGTCGGCCGCCTCTTGAGTGCTTTGGA    1080

D  L  Q  L  A  N  S  T  I  I  A  F  T  S  D  H  G  W  A  L    339
        *
CGATCTTCAGCTGGCCAACAGCACCATCATTGCATTTACCTCGGATCATGGGTGGGCTCT  1140

G  E  H  G  E  W  A  K  Y  S  N  F  D  V  A  T  H  V  P  L    359
AGGTGAACATGGAGAATGGGCCAAATACAGCAATTTGATGTTGCTACCCATGTTCCCCT   1200

I  F  Y  V  P  G  R  T  A  S  L  P  E  A  G  E  K  L  F  P    379
GATATTCTATGTTCCTGGAAGGACGGCTTCACTTCCGGAGGCAGGCGAGAAGCTTTCCC   1260
```

FIGURE 1-5

```
Y L D P F D S A S Q L M E P G R Q S M D        399
TTACCTCGACCCTTTGATTCCGCCCTCACAGTTGATGGAGCCAGGCAGGCAATCCATGGA  1320

L V E L V S L F P T L A G L A G L Q V P        419
CCTTGTGGAACTTGTGTCTCTTTTTCCCACGCTGGCTGGACTTGCAGGACTTGCAGGTTCC 1380

P R C P V P S F H V E L C R E G K N L L        439
ACCTCGCTGCCCCGTTCCTTCATTTCACGTTGAGCTGTGCAGAGAAGGCAAGAACCTTCT  1440

K H F R F R D L E E D P Y L P G N P R E        459
GAAGCATTTTCGATTCCGTGACTTGGAAGAGGATCCGTACCTCCCTGGTAATCCCCGTGA  1500
```

FIGURE 1-6

```
L  I  A  Y  S  Q  Y  P  R  P  S  D  I  P  Q  W  N  S  D  K      479
ACTGATTGCCTATAGCCAGTATCCCGGCCTTCAGACATCCCTCAGTGGAATTCTGACAA     1560

P  S  L  K  D  I  K  I  M  G  Y  S  I  R  T  I  D  Y  R  Y      499
                                    *
GCCGAGTTAAAAGATATAAAGATCATGGGCTATTCCATACGCACCATAGACTATAGGTA     1620

T  V  W  V  G  F  N  P  D  E  F  L  A  N  F  S  D  I  H  A      519
TACTGTGTGGGTTGGCTTCAATCCCTGATGAATTTCTAGCTAACTTTCTGACATCCATGC    1680

G  E  L  Y  F  V  D  S  D  D  P  L  Q  D  H  N  M  Y  N  D  S   539
                                                      *
AGGGAACTGTATTTGTGGATTCTGACCCCATTGCAGGATCACAATATGTATAATGATTC     1740
```

FIGURE 1-7

```
Q  G  G  D  L  F  Q  L  L  M  P                                        550
CCAAGGTGGAGATCTTTCCAGTTGTTGATGCCTTGAGTTTTGCCAACCATGGATGGCAA            1800
ATGTGATGTGCTCCCTTCCAGCTGGTGAGAGGAGTTAGAGCTGGTCGTTTTGTGATT             1860
ACCCATAATATTGGAAGCAGCCTGAGGGCTAGTTAATCCAAACATGCATCAACAATTTGG          1920
CCTGAGAATATGTAACAGCCAAACCTTTCGTTTAGTCTTTATTAAAATTATAATTGGT            1980
AATTGGACCAGTTTTTTTTAATTTCCCTCTTTTTAAACAGTTACGGCTTATTACTG              2040
AATAAATACAAAGCAAACTCAAGTTATGTCATACCTTTGGATACGAAGACCATACA              2100
TAATAACCAAACATAACATTATACACAAAGAATACTTTCATTATTGTGGAATTTAGTGC           2160
ATTTCAAAAAGTAATCATATATCAAACTAGGCACCACACTAAGTTCCTGATTATTTGTT           2220
TATAATTTAATAATATATCTTATGAGCCCTATATATTCAAAATATTATGTTAACATGTAA          2280
TCCATGTTTCTTTTCC                                                      2297
```

FIGURE 1-8

```
2                                    MPPPRTGRGLLWLGLVLSSVCVALGSETQANST
6                                             MGAPRSLLLALAAGLAVA
A                                 MGPRGAASLPRGPGPRRLLLPVVLPLLLLLLAPPGSGA
B                                            MPLRKMKIPFLLLFFLWEAES
C
U                              MKSAPFLFLLGLLGLVTAQTQDPALLDLLRENPDLLSLLLQSNEHR

2    TDALNVLLIIVDDLR-PSLGCYGDKLVRSPNIDQLASHSLLFQNAFAQQAVCAPSRVSFLTGR
6    TRRPNVVLLLTDDQD-EVLGGMTPLKKTKALIGEM---GMTFSSAYVPSALCCPSRASILTGK
A    RPPNIVLIFADDLGYDLGCYGHPSSTTPNLDQLAAGGLRFTDFYVPVSLCTPSRAALLTGR
B    GASRPPHLVFLLADDLGWNDVG-FHGSRIRTPHLDALAAGGVLLDNYYTQ-PLCTPSRSQLLTGR
C    HAASRPNIILVMADDLGIGDPGCYGNKTIRTPNIDRLASGGVKLTQHLAASPLCTPSRAAFMTGR
U    APLVKPNVVLLVADDMGSGDLTSYGHPTQEAGFIDKMAAEGLRFTNGYVGDAVCTPSRSAIMTGR
        *   *  *         *  *         *              *   *        ***
```

FIGURE 3-1

```
2  RPDTTRLYD------FN-----SYWRVHAGNFSTIPQYFKEN-GYVMMSVGK-VFHPGISSNHT
6  YPHNHHVVN-------NTLEGNCSSKSWQKIQEPNTFPAILRSMGYQIFFAGK-YLNEYGAPDA
A  LPVRMGMYP-------GVLV----PSSRGGLPLEEVTVAEVLAAR-GYLTGMAGK-WHLGVG---
B  YQIRTGLQH-------QIW-----PCQPSCVPLDEKLLPQLLKEA-GYTHMVGK-WHLGMY----
C  YPVRSGMASWSRTGVFL--FTASSGGLPTDEITFAKLLKDQ-GYSTALIGK-WHLGMSCHSK
U  LPVRIGTFG---ETRVFL---PWTKTGLPKSELTIAEAMKEA-GYATGMVGK-WHLGMNENSS
              *                  *     *              **   *    ****

2  DDSP------YSWSFPPYHPS--SEKYENTKTCRGPDGE----------------LHA
6  GGLEHVPL--GWSYWYALEKNS--KYYNYTLSINGKARK---------------H
A  PEGAFLPPHQGFHRFLGIPYSH-DQGPCQNLTCFPPATP---------------C
B  RKEC-LPTRRGFDTYFGYLLGS-EDYYSHERCTLIDAL----------------N
C  TDFCHHPLHHGFNYFYGISLTNLRDCKPGEGSVFTTGFKRLVFLPLQIVGVTLLTLA
U  TDGAHLPFNHGFD-FVGHNLPF-TNSWSCDDTGLHKDFP---------------D
              *     **

FIGURE 3-2
```

```
2  NLLCPVDVLDVPEGTLPDKQSTEQAIQLLEKMKTSASPFFLAVGYHKPHIPFRYPKEFQKLY
6  GENYSVDYLTDVLA------------------------------NVSLDF------LDYKSNFEPFF
A  DGGCDQGLVPIPL-----------------------------------------------
B  VTRC-----ALD------------------------------------------------
C  ALNC-LGLLHVPLG------------------------VFFSLLFLAALILTLFLGF----LHYFRPLNCF-
U  SQRC-----YL-------------------------------------------------
           *

2  ----PLENITLAPDPEVPDGLPPVAYNPWMDIRQR--EDVQALNISVPYGPIPVDF
6  MMIATPAPHSPWTAAPQYQKAFQNVFAPRNKNFNIH--GTNKHWLI---RQAKTPM
A  ----LANLSVEAQPPWLPGLEARYMAFAHDLMADAQRQDRPFFLYYASHHTHYPQ
B  ----FRDGEEVATGYKNMYSTNIFTKRAIALITN--HPPEKPLFLYLALQSVHEPL
C  ----MMRNYEIIQQPMSYDNLTQRLTVEAAQFIQ--RNTETPFLLVLSYLHVHTAL
U  ----YVNATLVSQPYQHKGLTQLFTDDALGFIED--NHADPFFLYVAFAHMHTSL
                  *                *           *      *
```

FIGURE 3-3

```
2  --------QRKIRQSYFASVSYLDTQVGRLLSALDDLQLANSTIAFTSDHGWALGE
6  TN------SSIQFLDNAFRKRW-QTLLSVDDLVEKLVKRLEFTGELNNTYIFYTSDNGYHTG-
A  --------FSGQSFAERSGRGPFGDSLMELDAAVGTLMTAIGDLGLLEETLVIFTADNGPETMR
B  QVPEEYLKPYDFIQDKNRHHYAGMVSLMDEAVGNVTAALKSSGLWNNTVFIFSTDNGGQTL-
C  --------FSSKDFAGKSQHGVYGDAVEEMDWSVGQILNLLDELRLANDTLIYFTSDQGAHVEE
U  --------FSSDDFSCTSRRGRYGDNLLEMHDAVQKIVDKLEENNISENTIFFISDHGPHREY
                                 *                            *

2  HGEWAKYSNFDVATHVPLIFYVPGRTASLPEAGEKLFPYLDPFDSASQLMEPGRQSM
6  -------QFSL----PIDKRQLYEFDIKV-----PLLVRGPGIK-PNQTSK
A  MS-----RGGCSGLL----RCGKGTTYEGGVRE-----PALAFWPGHIAPGVT-H
B  -------AGGNNWPL----RGRKWSLWEGGVRG-----VGFVASPLLKQKGVKNR
C  VSSKGEI----HGGSNGIY----KGGKANNWEGGIRV-----PGILRWPRVIQAGQKID
U  CE-----EGGDASIF----RGGKSHSWEGGHRI-----PYIVYWPGTISPGIS-N
    **            *        ***          *        *
```

```
2  DLVELVSLFPTLAGLAGLQVPPRCPVPSFHVELCREGKNLLKHEFRFRDLEEDPYLPGNPREL
6  MLVANIDLGPTILDIAGYDLNKT-QMDGMSL----------LPILRGASNLTWRSDVL
A  ELASSLDLLPTLAALAGAPLPNV-TLDGFDL----------RPPAAGHRQEPSAVSLL
B  ELIHISDWLPTLVKLARGHTNGTKPLDGFDV----------WKTISEGSPSP-RIELL
C  EPTSNMDIFPTVAKLAGAPLPEDRIIDGRDL----------MPLLEGKSQRSDHEFLF
U  EIVTSMDIIATAADLGTTLPTDRIYDGKSI----------KDVLLEGSASP-HSSFF
            *   *            *    **

2  IAYSQYPRPSDIPQWNSDKPSLKDIKIMGYSIRTIDYRYTVWVG-------------
6  VEYQGEGRNVTDPTCPSLSPGVSQCFPDCVCEDAYNNTYACVRTMSALW-NLQYC--
A  LPVLPRRGPWGFCCAD----WKVQGSLLHPGSAHSDTTAD----------PAC-
B  HNIDPNFVDSSPCPRNSMAPAKDDSSLPEYSAFNTSVHAAIRHGNWKLLTGYPGCGY
C  HYCNAYLNAVRWHPQNSTSIWKAFFFTPNFNPVGSNGCFAT---------HVC--
U  YYCKDNLMAVRVGKYKAHFRTQRVRSQDEYGLECAGG-FPL---------EDY-
```

```
2  -FNPDE--FLANFSDIHAGE-----LYFVDSDELQDHNMY--NDSQGGDLFQLLMP
6  ----------EFDDQEVFVEVYNLTADPDQITNI---AKTIDPELLGKMNYRLMMLQS
A  --------HASSSLTAHEPP---L--LYDLSKDPGENYNLLGGVAGATPEVLQALKQLQLLKAQ
B  WFPPPSQYNVSEIPSSDPPTKTLWLFDIDRDPEERHDL----SREYPHIVTKLLSRLQFYHKH
C  -F------CFGSYVTHHDPP---L--LFDISKDPRERNPL---TPASEPRFYEILKVMQEAADR
U  -FDCND-CEGDCVTEHDPP----L--LFDLHRDPGEAYPL--EACGHEDVFLTVKSTVEEHKAA
                           ** *   *  * **   *

2  CSGPTCRTPGVFDPGYR-FDPRLMF-------SNRGSVRTRRFSKHLL
6  LDAAVTFGPSQVARGE---DPALQICCHPGCTPRPACCHCPDPHA
A  SVPV--YFPAQ-------DPR-----CD-----PKATGVWGPWM
B  HTQTLPEVPDQFSWNNFLWKPWLQLCCP----STGLSCQCDREKQDKRLSR
C
U  LVKGTPLLDSFDHSIVPCCNPANGCICNYVHEPGMPECYQDQVATAARHYRP
                    *
```

FIGURE 3-6

```
gcgatctagacctagttagccaagtctctaacgtgacataggaaagcttgcaatggcaactggccgc
ccgtctcgcctgtctctgccacgcctattgctgcaggatgacgcacctctatgacccgccgtg
aggtgagtgtgacgcaggaagagtcgcacggacgcGctgccggccagctgcgggcccggg
cggcggctgtgttgcgcagtcttcatgggttcccgacgaggagtctctggctgcgggctgcta
actgcgccactgctgcccgcctctgaagcggccgctcgaagccgaa..exonI..
ATGCCGCCACCCCGAGGCCCTTCTCTGGCTCTGGTTCTGAGCTCCGTCTGCGTCGC
CCTCGGATCCGAAACGCAGGCCAACTCGACCACAGgtgccgccacgcccctgccatctctcctc
ccttcctctccttcctcctcctcttgttatcattcttttac
c.intronI...cccactcccaccctgctgaggcacagccctccctgctagctgttaggtgc
agggtccagcctgggccttagtaacctagcacctaccatgagggaggggttcagtgtcagtgcagg
```

FIGURE 7-1

```
ttacctcaccaagcccctcctcctgtgtag......exonII...ATGCTCTGAACGTTCTTCTCA
TCATCGTGGATGACCTGCGCCCCTCCCTGGGCTGTGTTATGGGGATAAGCTGGTGAGTCCCCAAATATT
GACCAACTGGCATCCCACAGCCTCCTCTTCCAGAATGCCTTTGCGCAGtatgtctggaacctctag
ctgtgggtgtgctgcttcgtgcactgagggttgggggcggggagcttcagctattgtcagatggca
cagattgtgcgggacatcttgttagagggaagcatagtctggaaa..intron2..agggcggttgct
tggttacctaagagatggcagacatctttgctgtggcgatgctacctctgctcctgctcctaaca
g......exonIII..CAAGCAGTGTGCGCCCCGAGCCGCGTTCTTCCTCACTGGCAGGAGACCTG
ACACCACCCGCCTGTACGACTTCAACTCCTACTGGAGGTGCACGCTGAAACTTCTCCACCATCCCC
CAGTACTTCAAGGAGAATGGCTATGTGACCATGTCGGTGGGAAAAGTCTTTCACCCTGtactgctcc
atgtccagagtctgggttctcttggtttgtggtgtctgantccagcattcccatcctgggatgggct
```

FIGURE 7-2

```
gtctttgcagagccctctctgctgggcgagtccctcgctagtcagtgct..intron3..tttgta
gatgaggaaactgagcccaaagaaggggagntccactgcccattgtttacagagtttaattatg
gggagtggggtgttgaaagactcatcatgttttaacaaccttttttttttccaag......exonIV
..GGATATCTTCTAACCATACCGATGATTCTCCGTATAGCTGGTCTTTCCACCTTATCATCCTTCCT
CTGAGAAGTATGAAAACACTAAGgtaaggctgtgaaaggacatttctgaagagaaccacttttcc
tttgtcacataaactactgggtatactgcatgtnctgtgaagctggttatataccgaagttgtggg
tttcatttgtgataatgttttgacagaagtaagt......intron4..tgttcagtctgagtgactta
acacgtgaagggctgattatgtgaacattaaatctgtgtgtgcttcatgctcatntcttgca
cttaaaagctgatgttatattattttgttttgaaag..exonV..ACATGTCGAGGGCCAGATGGAG
AACTCCATGCCAACCTGCTTTGCCCTGTGGATGTGCTGGAATGTTCCCGAGGGCACCTTGCCTGACAAA
```

FIGURE 7-3

```
CAGAGCACTGAGCAAGCCATACAGTTGTTGGAAAAGATGAAAACGTCAGCCAGTCCTTTCTTCCTGGC
CGTTGGGTATCATAAGCCACACATCCCCTTCAGATACCCCAAGgtgaagagctgttgagggctgatc
cagcacagctgtgacagctgtgttgttgagggagggatttgcacagggaggtggctacatcct
gccatcgccaggcaccatggttgcctgatgggcactagtgtcctcagtggagtaaagatgggatttag
aggt....intron5..aaaaggcagtatagacagtgattttcccccaag...exonVI...GAATTTCAGAAGTTGTATC
agagtgacaactttgtgctttgtggctttgtttttccccaag...exonVI...GAATTTCAGAAGTTGTATC
CCTTGGAGAACATCACCCCTGGCCCCCGATCCCGAGGTCCCTACCCCTGTGGCCTACAAC
CCCTGGATGGACATCAGGCAACGGGAAGACGTCCAAGCCTTAAACATCAGTGTGCCGTATGGTCCAAT
TCCTGTGGACTTTCAGgtatcaaggacataagtttggggatgtattggacactgatgacatagtgtcgt
aggtgaaaccactctctcagtagacacaactccacctataatgtcttattaagagctttctttgtgt
```

FIGURE 7-4

```
g..intron6..tagggattgggagagatgcacacggcaagcattatctctgtatgccttggcaattt
aaattgcagtcactctcattttttatttttcaattgcag.....exonVII..CGGAAAATCCGC
CAGAGCTACTTTGCCTCTGTGTCATATTTGGATACACAGGTCGGCCTCTTGAGTGCTTTGGACGA
TCTTCAGCTGGCCAACAGCACCATCATTACCTCGGATCATGgtaagcattttgaaattccct
ggtgagtcaaaacatctgaactttcctgtgaaacatgctttgcaaattgccattgacataaacatgg
gtgtg..intron7..tttcttctaggtgatgagtttctactcctctggttttttacaacaggaaatg
aaatggtatctaaaataaacagctgtggtatgattattcattctgtcattctgtgtcttta
tgaactag..exonVIII.GGTGGGCTCTAGGTGAACATGGAGAATGGGCCAAATACAGCAATTTGA
TGTTGCTACCCATGTCCCCTGATATTCTATGTTCCTGGAAGGACGGTTCACTTCCGGAGGCAGGCG
AGAAGCTTTCCCTTACCCTGACCCCTTTGATTCCGCCCTCACAGTTGATGGAGCCAGgtataaaatat
```

FIGURE 7-5

```
gctgaaatgatgattgcttgacagtaagatcaccttagtttatatgtgaaccacttattgaatcata
ggctttggggttacacagaccccc...intron8..aaagataaatggtgtaattaaaaaaagaaaac
atatggagcccagacaggtcctttactgctcctgctggccatggccaggctttatatgtaaccca
ttctgctctgtcgcttcctgtttcag..exonIX..GCAGGCAATCCATGGACCTTGTGGAACTTGTG
TCTCTTTTTCCCACGCTGGCTGGACTGCAGGACTGCAGGTTCCACCTGCTGCCCCGTTCCTTCATT
TCACGTTGAGCTGTGCAGAGAAGGCAAGAACCTTCTGAAGCATTTCGATTCCGTGACTTGGAAGAGG
ATCCGTACCTCCCTGGTAATCCCGTGAACTGATGCCTATAGCCAGTATCCCCGGCCCTTCAGACATC
CCTCAGTGGAATTCTGACAAGCCGAGTTTAAAAGATATAAAGATCATGGCTATTCCATACGCACCAT
AGACTATAGGTATACTGTGTGTGGGTTGGCTTCAATCCTGATGAATTTCTAGCTAACTTTTCTGACATCC
ATGCAGGGGAACTGTATTTTGTGGATTCTGACCCATTGCAGGATCACAATATGTATAATGATTCCCAA
```

FIGURE 7-6

```
GGTGGAGATCTTTTCCAGTTGTTGATGCCTTGAgttttgccaaccatggatggcaaatgtgatgtgct
ccttccagctggtgagaggaggagttagagctggtgtgtttgtgattacccatatattggaagcag
cctgagggctagttaatccaacatgcatcaacaattggcctgagaatatgtaacagccaaacttt
tcgtttagtctttattaaatttataattggtaattggaccagttttttttaattccctcttttt
aaaacagttacggcttattactgaataaatacaaagcaaacaaactcaagttatgtcatacctttgg
atacgaagaccatacataataaccaaacatatcaaactaggcaccacactagttcctgattattttgtt
tttagtgcatttcaaaagtaatcatataatatcttatgagccctatatattcaaaatatattgttaacatgtaatccatgtt
tataatttaataatatcttatgttaacatgtaacatgtaatccatgtt
tcttttcc
```

GLYCOSYLATION VARIANTS OF IDURONATE 2-SULFATASE

This is a divisional of copending application Ser. No. 08/345,212, filed on Nov. 28, 1994, which is a File Wrapper Continuation of U.S. Ser. No. 991,973 filed Dec. 17, 1992, which is a Continuation-in-part of U.S. Ser No. 790,362, filed Nov. 12, 1991 now abandoned.

FIELD OF THE INVENTION

The present invention relates to glycosylation variants of iduronate-2-sulfatase and to genetic sequences encoding same. The present invention also contemplates the use of these in the treatment and diagnosis of subjects suspected of, or suffering from, iduronate 2-sulfatase deficiency.

BACKGROUND TO INVENTION

Iduronate 2-sulfatase (hereinafter abbreviated to "IDS"; EC 3.1.6.13) acts as an exosulfatase in lysosomes to hydrolyze the C2-sulfate ester bond from non-reducing-terminal iduronic acid residues in the glycosaminoglycans heparan sulfate and dermatan sulfate (1). IDS is one of a family of at least nine sulfatases that hydrolyze sulfate esters in human cells. They are all lysosomal enzymes that act on sulfated monosaccharide residues in a variety of complex substrates with the exception of microsomal steroid sulfatase (or arylsulfatase C), which acts on sulfated 3β-hydroxysteriods (1,2). Each sulfatase displays absolute substrate specificity, making the sulfatase family an attractive model to investigate the molecular requirements for substrate binding and the catalysis of sulfate ester hydrolysis.

A deficiency in the activity of IDS in humans leads to the lysosomal accumulation of heparan sulfate and dermatan sulfate fragments and their excretion in urine (1). This storage results in the clinical disorder Hunter syndrome (mucopolysaccharidosis type II, MPS-II) in which patients may present with variable phenotypes from severe mental retardation, skeletal deformities, and stiff joints to a relatively mild course (1). It has been postulated that this clinical heterogeneity reflects different mutations at the IDS locus affecting enzyme expression, stability, or function. MPS-II is one of the most common mucopolysaccharidoes and is the only one that is X chromosome-linked (1).

In accordance with the present invention, there is provided the nucleotide sequence for a full length cDNA clone for IDS from human endothelial cells. The present invention also provides the genomic clone for IDS. More particularly, following expression of the IDS nucleotide sequence in particular cell lines, a glycosylation variant of IDS has been isolated which possesses inter alia improved half-life and/or improved uptake properties when compared to the naturally glycosylated molecule.

SUMMARY OF THE INVENTION

One aspect of the present invention provides a recombinant human iduronate 2-sulfatase (IDS) or a fragment thereof retaining enzymatic activity wherein said recombinant IDS or fragment thereof is more highly glycosylated than the naturally occurring enzyme or equivalent fragment on the naturally occurring enzyme.

Another aspect of the present invention contemplates a method for treating a patient suffering from iduronate 2-sulfatase (IDS) deficiency said method comprising administering to said patient an effective amount of a recombinant human IDS or a fragment thereof retaining enzymatic activity wherein said recombinant IDS or fragment thereof is more highly glycosylated than the naturally occurring enzyme or equivalent fragment on the naturally occurring enzyme.

Yet another aspect of the present invention is directed to a pharmaceutical composition useful in the treatment of patients suffering from iduronate 2-sulfatase (IDS) deficiency said composition comprising the more highly glycosylated IDS or enzymatically active fragment thereof referred to above and one or more pharmaceutically acceptable carriers and/or diluents.

Still yet another aspect of the present invention provides an isolated genomic DNA fragment carrying in whole or in part the IDS gene or a mutant or derivative thereof. The isolation of the genomic clone will enable gene therapy and genetic analysis of IDS deficiency diseases.

BRIEF DESCRIPTION OF THE FIGURES

FIG. 1 is a representation of compiled nucleotide sequence SEQ ID NO: 1 of the IDS cDNA clones and the deduced amino acid sequence of the encoded protein SEQ ID NO: 2. Amino acid sequence is shown in the one-letter code above the nucleotide sequence. Nucleotide and amino acid numbers are depicted on the right margin. Possible sites for peptidase cleavage of the signal peptide are indicated with arrows. Underlined amino acids are colinear with amino-terminal sequences (14 kDa, Pro-Arg-Glu-Leu-Ile-Ala-Tyr-Ser-Xaa-Tyr-Pro-Arg-Xaa-Xaa-Ile-Pro, SEQ ID NO: 3 determined by direct sequence analysis). Potential N-glycosylation sites are starred. A potential polyadenylylation signal is doubly underlined.

FIG. 3 is a representation showing alignment of amino acid sequences of human IDS, human glucosamine 6-sulfatase (19), human galactose 3-sulfatase or arylsulfatase A (14), human N-acetylgalactosamine 4-sulfatase or arylsulfatase B (15), human steroid sulfatase or arylsulfatase C (20, 21), and sea urchin arylsulfatase (22) shown in lines 2, 6, A, B C and U, respectively. Amino acids identical in all sulfatases are boxed. Amino acids identical in the arylsulfatase activities (lines A, B, C, and U) are starred on the bottom line. The ringed residues in lines 2, 6 and B indicate the first amino-terminal amino acid in polypeptides produced by internal proteolysis. Underlined sequences are unique to each particular sulfatase sequence and underlined and starred sequences are blocks of conserved residues.

FIG. 7 is a representation of the genomic nucleotide sequence for the IDS gene.

DETAILED DESCRIPTION OF THE INVENTION

Figures 2A, 2B:
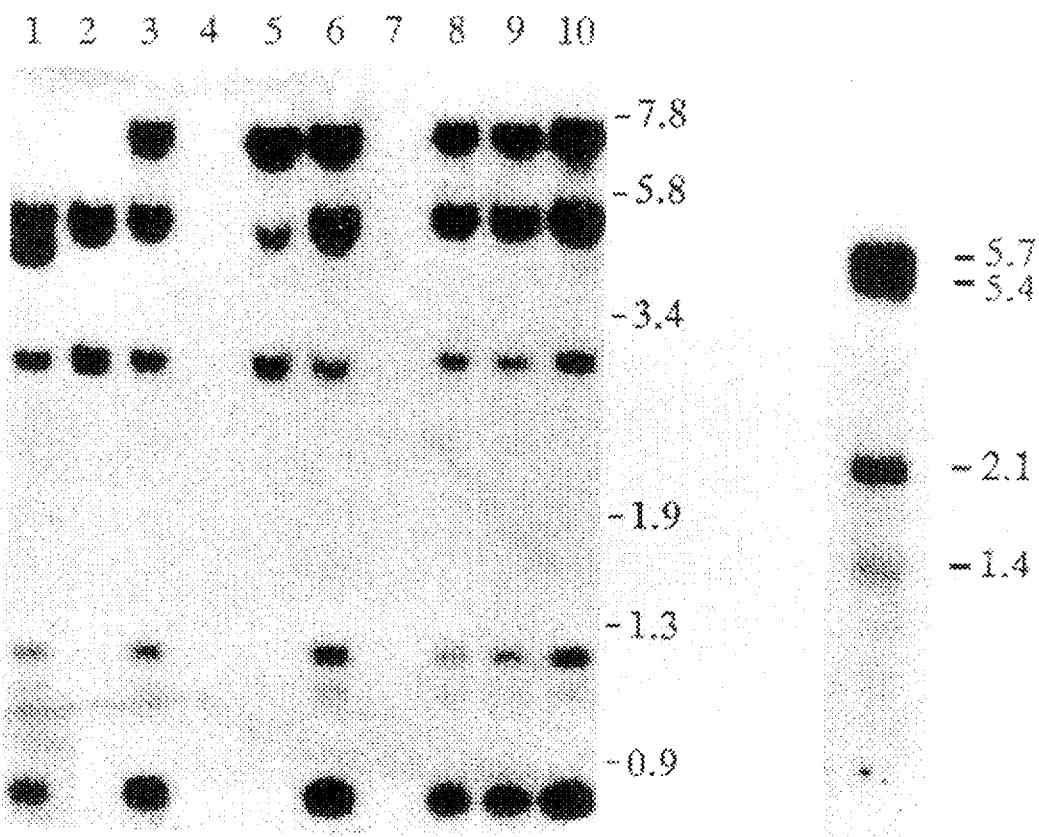
FIG. 2 is a photographic representation showing: (A) Southern blot analysis of MPS-II DNA for deletions and rearrangement of the IDS gene. λc2S15 was used to probe a Southern blot of Pst I-digested DNA samples from a normal male and female (lanes 9 and 10, respectively) and from severely affected MPS-II patients (lanes 1–8). The sizes (kb) of DNA molecular mass standards are shown in the right margin. (B) Northern blot of RNA from human placenta. The size (kb) of each RNA species is shown in the right margin.

The present invention provides an isolated nucleic acid molecule comprising a sequence of nucleotides which encodes or is complementary to a sequence which encodes human IDS or an enzymatically active fragment thereof. More particularly, the present invention is directed to the expression of such a nucleic acid molecule in a host cell which results in the recombinant IDS (rIDS) being more highly glycosylated relative to the extent of glycosylation of the naturally occurring molecule.

When comparing the extent of glycosylation, the reference molecule is either naturally occurring IDS purified, for example, from human liver or may be a recombinant molecule produced in a cell line with an extent of glycosylation similar to the naturally occurring molecule. The critical comparison is not the glycosylation pattern per se the extent to which the molecule is glycosylated.

Preferably, the more highly glycosylated IDS of the present invention has a molecular weight at least 5 kDa greater than the naturally occurring molecule or its recombinant equivalent, more preferably at least 10 kDa greater, even more preferably at least 15 kDa greater and still even more preferably at least 20-30 kDa greater. Accordingly, the more highly glycosylated IDS has a molecular weight of approximately 65-95 kD or more preferably from about 70 to about 90 kDa depending on the host cell employed. In a most preferred embodiment, the molecular weight is about 90 kDa when produced in CHO-K1 cells or about 70 kDa when produced in CHO-Lec 1 cells.

Conveniently, the cDNA encoding IDS or its fragment is modified by replacing the 5' non-coding sequence with a portion of rat pre-pro-insulin leader sequence and inserted into an appropriate expression vector. The modified cDNA is then subject to expression in cell lines capable of more highly glycosylating the resulting recombinant molecule. Although the preferred cell lines described herein are CHO-KI cells and CHO-Lec1 cells, it would be routine for one skilled in the art to select other cell lines and screen the resulting recombinant IDS to ascertain the extent of glycosylation. All cell lines resulting in a more highly glycosylated IDS are encompassed by the present invention.

The "nucleic acid molecule" of the present invention may be RNA or DNA (eg. cDNA), single or double stranded and linear or covalently closed. The nucleic acid molecule may also be genomic DNA corresponding to the entire gene or a substantial portion thereof or to fragments and derivatives thereof. The nucleotide sequence may correspond to the naturally occurring nucleotide sequence or may contain single or multiple nucleotide substitutions, deletions and/or additions including fragments thereof. All such variations in the nucleic acid molecule retain the ability to encode a more highly glycosylated IDS when expressed in the appropriate host or an enzymatically active fragment of IDS. The enzymatic activity of the resultant molecule is readily ascertained by, for example, using the radiolabelled disaccharide substrate ldoA2S-anM6S of Bielicki et al (3).

The nucleic acid molecule of the present invention may constitute solely the nucleotide sequence encoding human IDS or like molecule or may be part of a larger nucleic acid molecule and extends to the genomic clone of IDS. The non-IDS encoding sequences in a larger nucleic acid molecule may include vector, promoter, terminator, enhancer, replication or signal sequences or non-coding regions of the genomic clone.

In its most preferred embodiment, the cDNA encoding IDS SEQ ID NO: 1 is as set forth in FIG. 1 or having at least 60%, preferably at least 70% and even more preferably at least 80-90%, similarity thereto. The genomic sequence encoding IOS is SEQ ID NO: 6 preferably as set forth in FIG. 7 or having similarity thereto as defined above for the cDNA clone.

The present invention is particularly directed to recombinant IDS in more highly glycosylated form as hereinbefore described. The recombinant IDS may comprise an amino acid sequence corresponding to the naturally occurring amino acid sequence or may contain single or multiple amino acid substitutions, deletions and/or additions. The present invention also extends to fragments of the IDS molecule but which retain IDS activity. Such fragments are referred to herein as being "enzymatically active". Accordingly, this aspect of the present invention contemplates a highly glycosylated IDS molecule or enzymatically active fragments or derivatives thereof. The IDS molecule of the present invention, therefore, comprises parts, derivatives and/or portions of the IDS enzyme having enzymatic activity and being more highly glycosylated relative to the naturally occurring enzyme or equivalent fragment or derivative.

Advantageously, the recombinant highly glycosylated IDS is a biologically pure preparation meaning that it has undergone some purification away for other proteins and/or non-proteinacous material. The purity of the preparation may be represented as at least 40% of the enzyme, preferably at least 60%, more preferably at least 75%, even more preferably at least 85% and still more preferably at least 95% relative to non-IDS material as determined by weight, activity, amino acid homology or similarity, antibody reactivity or other convenient means.

Amino acid insertional derivatives of IDS of the present invention include amino and/or carboxyl terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in the sequence has been removed and a different residue inserted in its place. Typical substitutions are those made in accordance with the following Table 1:

TABLE 1

| Suitable residues for amino acid substitutions | |
|---|---|
| Original Residue | Exemplary Substitutions |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Where the enzyme is derivatised by amino acid substitution, the amino acids are generally replaced by other amino acids having like properties such as hydrophobicity, hydrophilicity, electronegativity, bulky side chains and the like. Amino acid substitutions are typically of single residues. Amino acid insertions will usually be in the order of about 1–10 amino acid residues and deletions will range from about 1–20 residues. Preferably, deletions or insertions are made in adjacent pairs, i.e. a deletion of two residues or insertion of two residues.

The amino acid variants referred to above may readily be made using peptide synthetic techniques well known in the art, such as solid phase peptide synthesis (Merrifield synthesis) and the like, or by recombinant DNA manipulations. Techniques for making substitution mutations at predetermined sites in DNA having known or partially known sequence are well known and include, for example, M13 mutagenesis. The manipulation of DNA sequence to produce variant proteins which manifest as substitutional, insertional or deletional variants are conveniently elsewhere described such as Sambrook et al, 1989 *Molecular Cloning: A Laboratory Manual* Cold Spring Harbor Laboratories, Cold Spring Harbor, N.Y.

The derivatives of the IDS of the present invention include single or multiple substitutions, deletions and/or additions of any component(s) naturally or artificially associated with the IDS enzyme such as carbohydrate, lipid and/or other proteinaceous moieties. All such molecules are encompassed by the expressions "mutants", "derivatives", "fragments", "portions" and "like" molecules. These molecules are enzymatically active and retain their more highly glycosylated form relative to the naturally occurring enzyme or equivalent derivative when produced in suitable host cells.

The present invention also extends to recombinant IDS molecules when fused to other proteinaceous molecules. The latter may include another enzyme, reporter molecule, purification site or an amino acid sequence which facilitates transport of the molecule out of a cell.

In a most preferred embodiment, the present invention has an amino acid or corresponding IDS cDNA nucleotide sequence substantially as setforth in FIG. 1 or having at least 40% similarity, preferably at least 60% similarity thereto or more preferably at least 80% or 85–90% similarity thereto.

The present invention further contemplates antibodies to the more highly glycosylated IDS. The antibodies may be polyclonal or monoclonal, naturally occurring or synthetic (including recombinant, fragment (eg Fab Fragment) or fusion forms). Such antibodies will be useful in developing immunoassays for IDS and in distinguishing between molecules having an altered extent of glycosylation. Preferably, therefore, the antibody is capable of binding the more highly glycosylated form of IDS but not the naturally glycosylated form of the molecule.

It is within the scope of this invention to include any second antibodies (monoclonal, polyclonal or fragments of antibodies) directed to the first mentioned antibodies discussed above. Both the first and second antibodies may be used in detection assays. Furthermore, the first antibody may be used with a commercially available anti-immunoglobulin antibody. An antibody as contemplated herein includes any antibody specific to the more highly glycosylated form of IDS but not to the normally glycosylated enzyme.

Both polyclonal and monoclonal antibodies are obtainable by immunization with the enzyme or protein and either type is utilizable for immunoassays. The methods of obtaining both types of sera are well known in the art. Polyclonal sera are less preferred but are relatively easily prepared by injection of a suitable laboratory animal with an effective amount of IDS, or antigenic parts thereof, collecting serum from the animal, and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example Douillard and Hoffman, Basic Facts about Hybridomas, in *Compendium of Immunology Vol II, ed. by Schwartz,* 1981; Kohler and Milstein, *Nature* 256: 495–499, 1975; *European Journal of Immunology* 6: 511–519, 1979). Antibodies capable of also binding to the non-highly glycosylated form of IDS can be readily removed, for example, by immuno-adsorbant techniques.

The assay for the highly glycosylated IDS may be accomplished in a number of ways such as by Western blotting and ELISA procedures. A wide range of immunoassay techniques are available as can be seen by reference to U.S. Pat. Nos. 4,016,043, 4,424,279 and 4,018,653. These, of course, include both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist, and all are intended to be encompassed by the present invention. Briefly, in a typical forward assay, an unlabelled antibody is immobilized on a solid substrate and the samples containing an IDS to be tested is brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. In accordance with the present invention, the sample is generally a biological sample comprising biological fluid but also extends to fermentation fluid and supernatant fluid such as from a cell culture.

In the typical forward sandwich assay, a first antibody having specificity for the highly glycsylated IDS, or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer antibody complex is washed in preparation for the test sample. An aliquot of the sample to be tested is then added to the solid phase complex and incubated for a period of time sufficient (e.g. 2–40 minutes) and under suitable conditions (e.g. 25° C.) to allow binding of any subunit present in the antibody. Following the incubation period, the antibody subunit solid phase is washed and dried and incubated with a second antibody specific for a portion of the hapten. The second antibody is linked to a reporter molecule which is used to indicate the binding of the second antibody to the hapten.

An alternative method involves immobilizing the target IDS molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to one skilled in the art. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorecein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Imnmunofluorescene and EIA techniques are both very well established in the art and are particularly preferred for the present method. However, other reporter molecules, such as radioisotope, chemiluminescent or bioluminescent molecules, may also be employed.

The present invention further contemplates a method of treating a patient suffering from IDS deficiency said method comprising administering to said patient an effective amount of a recombinant human IDS or a fragment thereof retaining enzyme activity wherein said recombinant IDS or fragment thereof is more highly glycosylated than the naturally occurring enzyme or equivalent fragment of the naturally occurring enzyme.

The highly glycosylated rIDS has enhanced uptake properties and/or a longer in vivo half-life and, hence, is more effacacious than the naturally glycosylated molecule.

Such a highly glycosylated IDS is as herein described. Generally, this aspect of the present invention can be accomplished using a pharmaceutical composition.

Accordingly, another aspect of the present invention contemplates a pharmaceutical composition useful in treating patients suffering from a deficiency in IDS such as in Hunter Syndrome, said composition comprising a recombinant human IDS or a fragment thereof retaining enzyme activity wherein said recombinant IDS or fragment thereof is more highly glycosylated than the naturally occurring enzyme or equivalent fragment of the naturally occurring enzyme, said composition further comprising one or more pharmaceutically acceptable carriers and/or diluents.

The formulation of pharmaceutical composition is generally known in the art and reference can conveniently be made to Remington's Pharmaceutical Sciences, 17th ed., Mack Publishing Co., Easton, Pa., USA.

The active ingredients of a pharmaceutical composition comprising the highly glycosylated IDS or fragments thereof are contemplated to exhibit excellent therapeutic activity, for example, in treating Hunter Syndrome when administered in amount which depends on the particular case. For example, from about 0.5 µg to about 20 mg per patient or per kilogram of body weight of the patient per day, week, or month may be administered. Dosage regima may be adjusted to provide the optimum therapeutic response. For example, several divided doses may be administered daily or the dose may be proportionally reduced as indicated by the exigencies of the therapeutic situation. Depending on the patient or other conditions more preferred dosages comprise 10 µg to 10 mg, 20 µg to 5 mg or 100 µg per patient or per kilogram of body weight of the patient per administration. The composition may be administered an any convenient manner such as by the oral, intravenous (where water soluble), intramuscular, subcutaneous, intranasal, intradermal or suppository routes or implanting (eg using slow release molecules). Depending on the route of administration, the active ingredient which comprises a highly glycosylated IDS or fragment thereof may be required to be coated in a material to protect said ingredients from the action of enzymes, acids and other natural conditions which may inactivate said ingredients. For example, due to the low lipophilicity of IDS, these may potentially be destroyed in the gastrointestinal tract by enzymes capable of cleaving peptide bonds and in the stomach by acid hydrolysis. In order to administer the IDS molecules by other than parenteral administration, they may be coated by, or administered with, a material to prevent its inactivation. For example, the IDS molecules may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DFP) and trasylol. Liposomes include water-in-oil-in-water emulsions as well as conventional liposomes.

The active compounds may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as licithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thirmerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the highly glycosylated recombinant IDS molecules are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains an effective amount of recombinant IDS as hereinbefore described.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavoring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/ or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent oil (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 µg to about 2000 mg includes 1.0 µg to 20 mg. 10 µg to 2 mg and 100 µg to 10 mg. In the case of compositions containing supplementary active ingredients, the dosages are determined by reference to the usual dose and manner of administration of the said ingredients.

EXAMPLE 1

CLONING OF IDS GENE

1. MATERIALS AND METHODS

Materials

Form A of IDS was purified from human liver as described (3). Restriction endonucleases, polynucleotide kinase, T4 DNA ligase, the Klenow fragment of DNA polymerase I, and M13 sequencing kits were from Boehringer Mannheim. GeneScreeen Plus nylon filters were from DuPont/NEN. [$\gamma$-$^{32}$P]ATP (500 Ci/mmol; 1 Ci=37 GBq), [$\alpha$-$^{32}$P]dCTP (3000 Ci/mmol), and Multiprime DNA labeling kit were from Amersham. Oligo(dT)-cellulose and Sephadex G-50 were from Pharmacia P-L Biochemicals. The X chromosome genomic library LA0XNL01 was from the American Tissue Culture Collection, and the $\lambda$gt10 random-primed human colon cDNA library (1.5×10$^6$ independent clones) and the $\lambda$gt11 human endothelial cDNA library (2.1×10$^6$ independent clones) were from Clontech.

Polypeptide Isolation and Sequencing

Approximately 20 µg of form A liver IDS was subjected to a SDS/polyacrylamide gel electrophoresis and transferred to an Immobilon P membrane (Millipore) (4) with modifications of overnight pre-electrophoresis of the SDS/polyacrylamide gel and the addition of 200 µl of 100 mM sodium thioglycollate to the cathode buffer chamber before electrophoresis. The 42-kDa and the 14-KDa polypeptides were excised and directly amino-terminal sequenced by Bresatec (Adelaide, Australia).

Library Screening

A 49-mer oligonucleotide sequence SEQ ID NO: 4 (3'-ACTAGTAGCACCTGCTGGACGCCGG-GACGGACCCGCTGATGCTGCT GCA-5') was designed from the amino-terminal amino acid sequence SEQ ID NO: 5 (using residues 8-24 of TSALNVLLIIVDDLRPSLGDYDDVL) of the 42-kDa IDS polypeptide. T4 polynucleotide kinase and [$\gamma$-$^{32}$P]ATP were used to end-label the 49-mer to a specific activity greater than 10$^7$ cpm/µg for screening of the X chromosome library. The bacterial host used was NM538 and 2×10$^5$ recombinants were screened at a density of 30,000 plaque-forming units per 15 cm plate. Positive clones were plaque-purified, DNA was isolated from lysates, and the inserts were separated on 1% w/v agarose and then analysis by Southern blotting using the labeled 49-mer as a probe. A 49-mer positive 1.6-kilobase (kb) HindIII genomic DNA fragment was labeled with [$\alpha$-$^{32}$P]dCTP using a Multiprime DNA labelling kit and used to screen the human colon cDNA library. Approximately 5×10$^5$ recombinants were screened at a density of 55,000 plaque-forming units per 15 cm plate using the bacterial host C600. A 300-base-pair (bp) HindIII-EcoRI fragment from the 3' end of a 1.5-kb colon cDNA clone ($\lambda$c2S15) was labelled and used to screen the human endothelial cDNA library. The bacterial host used was NM538 and 5×10$^5$ recombinants were screened at a density of 40,000 plaque-forming units per 15 cm plate.

Nucleotide Sequencing

Sonicated DNA fragments generated from the 1.5-kb cDNA insert were subcloned into M13mp19 for nucleotide sequence analysis by the dideoxynucleotide chain-termination method by using the Klenow fragment of DNA polymerase I at 45° C. (5). Some internal regions of the 1.5-kb cDNA were sequenced using primers labeled at their 5' ends with [$\lambda$-$^{32}$P]ATP with single-stranded DNA templates generated by asymmetric polymerase chain reactions. The remaining coding sequence and the 5' and 3' untranslated regions present on the 2.3 kb endothelial cDNA were sequenced using specific primers on M13 subclones.

Southern Blot Analysis of MPS-II Patients

DNA from MPS-II patients and normal control cultured fibroblasts was prepared and digested with Pst I (6) and separated by agarose gel electrophoreses and transferred to GeneScreen Plus nylon membrane. The cDNA fragment $\lambda$c2S15 was radiolabeled using the Multiprime DNA labeling kit and purified by gel filtration on a 1-ml Sephadex G-50 column. The nylon filter was prehybridized, hybridized, and washed according to the manufacturer's instructions.

RNA Isolation and Nothern Blot Analysis

Total RNA was isolated from placental tissue by using a single-step guanidinium thiocyanate method (7). Poly(A)$^+$ RNA was obtained by oligo(dT)-cellulose chromatography and characterized by Northern Blot analysis carried out after electrophoresis in a 0.8% w/v agarose/2.2M formaldehyde gel and transfer to GeneScreen Plus nylon membrane. Prehybridization, hybridization, and washing were performed according to the manufacturer's instructions. Radiolabeled $\lambda$c2S15, prepared and purified as described above, was used in all hybridization experiments.

Sequence Analysis

The nucleotide sequence was screened against the GenBank nucleotide sequence data base (Release 62.0, December 1989) and the encoded protein sequence was screened against the National Biomedical Research Foundation protein data base (Release 23.0, December 1989). General sequence analysis and the multiple protein sequence alignment were performed using programs from Reisner and Bucholtz (8) and Lipman et al. (9), respectively.

2. RESULTS

IDS from human liver can be purified to two major forms (A and B) which have different pI values and contain both 42 kDa and 14 kDa polypeptides (3). The 42 kDa and 14 kDa polypeptides in form A were subjected to direct amino-terminal amino acid sequencing and a region of low codon redundancy in the 42 kDa amino-terminal sequence was used to design a single 49-mer oligonucleotide sequence incorporating choices based on human codon usage (10). The 49-mer detected 14 clones when used to screen an X chromosome enriched genomic library. Two overlapping clones were analysed in more detail and found to contain the same 1.6 kb 49-mer positive HindIII fragment. This fragment was shown to give a positive signal when used to probe DNA from a human-mouse cell hybrid that contained the tip of the long arm of the X chromosome (Xq26-ter) consistent with the localisation of the IDS gene to this small portion of the human X chromosome (1).

The 1.6 kd HindIII genomic DNA fragment was then used to screen a human colon cDNA library. Eighteen clones were detected and their inserts were sized. The clone with the longest insert (λ2S15) was fully sequenced and found to contain an initiating methionine and a continuous open reading frame that included a sequence that was colinear with the 42 kDa and the 14 kDa amino-terminal amino acid sequences. However, the reading frame did not extend to include a stop codon or any 3' untranslated region. A 300 bp HindIII-EcoRI restriction fragment from the 3' end of the λc2S15 was then used to screen a cDNA library constructed from human endothelial cells. Twenty seven clones were isolated; 5 of which were also positive to the amino-terminal-specific 49-mer. Of the five, the clone that contained the longest insert (2.3 kb; λc2S23) was sequenced in combination with λc2S15.

FIG. 1 (SEQ ID NO: 1) shows the nucleotide sequence of the 2297 bp insert from λ2S23, which encodes the entire amino acid sequence of IDS. Except for a few differences, the deduced amino acid sequence was colinear with the determined amino-terminal amino acid sequence of the 42 kDa and 14 kDa polypeptides. The amino acid discrepancies (residues 35, 53, 55 and 57) between the direct and predicted amino acid sequence data are believed to reflect amino acid sequencing errors resulting from the low signal obtained toward the end of the amino acid sequencing run. The detection of gene deletions and rearrangements in DNA from a group of severely affected MPS-II patients when hybridised with λc2S15 established that these cDNA clones encoded IDS (FIG. 2A). Of the 23 MPS-11 patients analysed, 7 had structural alterations including deletions of the entire Ac2S15 coding region. These 7 patients also revealed similar Southern patterns indicative of structural alterations of the IDS gene when their DNA was digested with HindIII, Stu I and Taq I and probed with λc2S15. Sixteen patients had identical patterns to normal controls, suggesting the presence of small deletions or point mutations responsible for the MPS-II biochemical and clinical phenotype. The two patients, in which the entire IDS gene had been removed (FIG. 2A) had the most severe clinical phenotype of the large group of MPS-II patient studied, raising the possibility that these patients may also have deletions of contiguous genes to IDS.

The sequence of λc2S23 shown in FIG. 1 (SEQ ID NO: 1) contains an open reading frame from the initiation codon at position 125 to the termination codon (TGA) at position 1775. This 1650 bp sequence encodes a polypeptide of 550 aminno acids (SEQ ID NO: 2) as shown.

The sequence flanking the ATG codon at bp 125 of SEQ ID NO: 1 is in agreement with the consensus sequence for initiator codons (11). The first 25 amino acids at the amino terminus of the deduced protein have features characteristic of a signal sequence (12). Two putative sites for cleavage between the signal sequence and mature protein are indicated by arrows (FIG. 1). It would appear that eight amino acids are removed from the IDS precursor immediately after the most favored signal peptidase cleavage site (12) between residues 25 and 26. The 14 kDa polypeptide amino-terminal amino acid sequence was identified at amino acid residue 456, giving a total of 95 amino acids to the carboxyl terminus. The full sequence contains eight possible N-glycosylation sites (Asn-Xaa-Ser/Thr, FIG. 1). The molecular weight of the deduced polypeptide for the 14 kDa component was calculated as 11.093. The 14 kDa polypeptide does not contain cysteine residues, which is compatible with the finding that the 42 kDa and the 14 kDa polypeptide are not linked by disulfide bonds (3). The number of potential N-glycosylation sites used in the 42 kDa polypeptide is not known. The first N-glycosylation site (residue 31) is not contained within IDS form A since this asparagine residue is removed during amino-terminal processing. The molecular weight of the deduced peptide for the 42 kDa component was calculated as 47, 404, suggesting that the value determined by SDS/polyacrylamide gel electrophoresis (3) may be in error or that additional amino acids are lost during internal proteolytic cleavage of the IDS precursor. These results suggest that post-translational proteolytic processing of IDS is restricted to cleavage of a signal peptide, removal of the amino-terminal 8 amino acids, and internal cleavage to produce the observed 42 and 14 kDa polypeptides in human liver, kidney, lung and placenta (3). This is a commonly observed polypeptide maturation process for lysosomal enzymes that are generally synthesised as larger precursors and then coverted to their mature forms by a limited number of proteolytic steps shortly before or after their transfer into lysosomes (13).

Northern blot analysis of placental poly (A)$^+$ t RA with λc2S15 revealed three major RNA species (5.7, 5.4 and 2.1 kb) and one minor species (1.4 kb) (FIG. 2B). It is likely that IDS, like other lysosomal enzymes [e.g., arylsulfatase A, B, and C (14–16)], has mRNA species that differ in length at their 3' ends due to differential polyadenylation. Arylsulfatase C has three major RNA transcripts that result from the use of different polyadenylation sites (2.7, 5.2 and 7.0 kb) the longest of which has a 3' untranslated region of >4 kb (16). Differential polyadenylation can account for the three major species but it cannot explain the 1.4 kb minor species, which is too small to encode the full IDS protein. It is possible tha the 1.4 kb species represents a degradation produce or a cross-reacting species, although it is also possible that is results from a process of differential splicing to produce another protein product, as has been observed for the human lysosomal enzymes, for example, β-glucuronidase (17) and β-galactosidase (18). The 520 bp of 3' untranslated region in λc2S23 contains a potential polyadenylation signal (AATAAA) at position 2041 that may direct the position of polyadenylation for the observed 2.1 kd) mRNA species. If this is the case, the 124 bp of 5' untranslated region in λc2S23 is sufficient to account for most, if not all, of the 5' untranslated region expected for the 2.1 kb mRNA species [allowing for 50–100 residues of poly(A) tail].

FIG. 3 shows an alignment of IDS amino acid sequence with sequence of other human-derived sulfatases and a sea urchin arylsulfatase. This analysis reveals many areas of identical and conserved amino acid matches within the arylsulfatase group (galactose 3-sulfatase, N-acetylgalactosamine 4-sulfatase and steroid sulfatase) and the two nonarylsulfatase sequences (unpublished data), IDS and glucosamine 6-sulfatase. Sea urchin arylsulfatase is also aligned and has sequence homology with the other five human sulfatases. A multiple sequence alignment of the amino acid sequence of these six sulfatases has the highest level of homology in the amino-terminal third of each sulfatase (FIG. 3). The human arylsulfatase group has conserve blocks of up to six identical amino acid residues, for example, Cys-Thr-Pro-Ser-Arg and Gly-Lys-Trp-His-Leu- Gly (FIG. 3). On the other hand, only part of these sequences are conserved in the two nonarylsulfatases, IDS and glucosamine 6-sulfatase. These sequences may represent regions of the arylsulfatases that enable the relatively nonspecific hydrolysis of arylsulfates. All five human sulfatases have significant sequence homology with the amino acid sequence of sea urchin arylsulfatase (FIG. 3). By taking account of conservative amino acid substitutions (23), there are even larger areas of homology within these six sulfatases. This high level of sequence conservation further supports the suggestion that these five human sulfatases are evolutionarily related to a common ancestral gene (14, 15, 19).

There are several regions in FIG. 3 where peptide inserts appear to be unique to a particular sulfatase. For instance, the microsomal membrane-bound steroid sulfatase contains two membrane-spanning regions (FIG. 3) (21). IDS also contains an amino acid sequence insert in the same region as the second membrane-spanning region of steroid sulfatase (FIG. 3). A second peptide insert in IDS is present just before the amino terminal sequence of the 14 kDa polypeptide. The role that these two peptide inserts may have in IDS function is unknown. Interestingly, the sites (ringed in FIG. 3) for internal proteolysis of both glucosamine 6-sulfatase (19) and N-acetylgalactosamine 4-sulfatase also occur near the sequence inserts.

The genomic sequence for IDS was isolated and is set forth in FIG. 7 (and SEQ ID NO: 6).

EXAMPLE2

PRODUCTION OF HIGHLY GLYCOSYLATED FORMS OF IDS

1. MATERIALS AND METHODS

All enzymes for DNA manipulations, DNAase, dithiothreitol, kanamycin and streptomycin were purchased from Boehringer Mannheim (Dulwich, SA, Australia). DNA oligonucleotidues were synthesised using an Applied biosystems 391 DNA Synthesiser. $Na_2^{35}SO_4$ (516 mCi/mmol) was purchased from New England Nuclear (Dupont, North Ryde, NSW, Australia). PBE94 chromatofocusing medium, polybuffer 74 and high and low molecular-mass standard kits for SDS-PAGE and gel chromatography were obtained from Pharmacia (North Ryde, NSW, Australia). TSK G3000SW Ultrapac was purchased from LKB (Bromma, Sweden). Blue A matrix agarose gel and ultrafiltration stirred cell model 8200 and Diaflo ultrafiltration membrane YM10 was obtained from Amicon (Danvers, Mass., USA). Dialysis membrane with a 10–12 kDa cut off was obtained from Union Carbide Corp. (Chicago, Ill., USA). Endoglycosidase F was purchased from Nenzymes (DuPont Co., Wilmington, Del. USA). Dulbecco's modified phosphate-buffered saline (PBS) was purchased from Commonwealth Serum Laboratories (Melbourne, Vic, Australia). Nonidet P40, mannose-6-phosphate and BSA were purchased from Sigma (St. Louis, Mo., USA). Basal medium Eagle's (BME), penicillin and glutamine were obtained from Flow Laboratories (Sydney, NSW, Australia) and fetal calf serum (FCS), Ham's F12 nutrient mixture, CHO-SFM medium and G418 (Geneticin) were from Gibco (Glen Waverley, Vic., Australia).

DNA Manipulation and Recombinant Plasmids

All DNA preparation, modification and cloning procedures were done using standard techniques (26). The IDS cDNA clone pB12Sc17 contains bp 107 (NotI restriction enzyme site) to bp 1870 (BstXI restriction enzyme site) of the IDS cDNA of Example 1 (SEQ ID NO: 1), cloned between the NotI and EcoRV restriction enzyme sites of pBlueScript (Stratagene, La Jolla, Calif. USA). The expression vector pRSVN.08 was derived from pRSVN.07 (27) by the introduction of an EcoRV site into the polylinker such that the order of restriction sites is 5' HindIII, XbaI, BamHI, EcoRV, EcoRI, NotI 3'.

Culture and Electroporation of CHO-K1 cells

CHO-K1 cells were cultured and electroporated as previously described (17) unless otherwise stated. Lec 1 cells are available from the New Jersey Cell Line Collection, New Jersey, USA. Under ATCC CRL 1735 and are described Culture of fibroblasts Human diploid fibroblasts were established from skin biopsies submitted to this hosptial for diagnosis (28). Cell lines were maintained according to established procedures in BME, 10% v/v FCS and antibiotics unless otherwise stated. The two MPS II skin fibroblast cell lines used in this study (SF-635 and SF-1779) both have low residual IDS activity.

Determination of IDS expression

Media samples, or cell lysates prepared by six cycles of freeze/thaw in 0.5M-NaCl/20 mM-Tris/HCl, pH 7.0, were clarified by microcentrifugation (12,000×g, 4° C., 5 min) and were either assayed directly or after dilution in assay buffer. Where possible cell lysates were dialysed in 5 mM-sodium acetate, pH 4.0, before assaying as this results in higher measured enzyme activity. IDS was assayed using the radiolabelled disaccharide substrate IdoA2S-anM6S (3). Protein estimations were according to the method of Lowry et al (29).

β-Hexosamidase

The fluorogentic substrate 4-methylumbelliferyl-2-acetamido-2-deoxy-β-D-glucopyranoside was used to measure β-hexosaminidase activity (31).

Correction of MPS II fibroblasts

For these experiments IDS was obtained from CHOEFI2S-9 cells cultured in CHO-SFM medium supplemented with 10 mM-$NH_4Cl$ and antibiotics. The medium was concentrated 10-fold by ultrafiltration and was shown to contain rIDS with activity of $2.75 \times 10^6$ pmol/min per ml (133 μg of I2S/ml). Fibroblasts from a normal individual (SF-3409) and from two MPS II patients (SF-635 and SF-1779) were grown to confluency in 25 $cm^2$ flasks and radiolabelled with $Na_2^{35}SO_4$ as previously described (27). The labelled cells were then exposed to $5 \times 10^4$ pmol/min per ml of rIDS for 72 hours. After harvesting the cells by trypsin treatment and washing by centrifugation/resuspension in PBS, the cell pellet was resuspended in 100 μl of 20 mM-Tris/HCl, pH 7.0/0.5M-NaCl, and the cell lysates prepared as described above. The cell extracts were analysed for IDS activity, total protein, β-hexosaminidase activity and radioactivity.

Endocytosis of rIDS

Cells from SF-1779 were plated in 20 wells (3.83 $cm^2$) and allowed to reach confluency. Well 1 to 4 were untreated controls. To each of wells 5 to 12 and 13 to 20 was added 1.0 ml of medium containing rIDS at $5 \times 10^4$ pmol/min per ml and $5 \times 10^3$ pmol/min per ml respectively. In addition the medium in wells 9 to 12 and 17 to 20 was made 5 mM mannose-6-phosphate. The cells were then incubated for 6 hours after which time they were rinsed with medium and fresh medium added. The cells were incubated overnight and then harvested, washed and lysed as described above. The cell lysates were dialysed against 5 mM-sodium acetate, pH 4.0, for 16 h at 4° C. and then analysed for IDS activity and total protein.

Subcellular fractionation

Cells from SF-635 were grown to confluency in 75 cm$^2$ flasks and then exposed to medium supplemented with $5\times10^4$ pmol/min per ml rIDS. The cells were incubated for 72 h then harvested and fractionated on Percoll density gradients as described in Anson et al (27). The resulting gradient was collected in 1.0 ml fractions by bottom puncture and the fractions analysed for IDS and β-hexosaminidase activity.

Large-scale production of rIDS

CHOEFI2S-9 cells were inoculated into two 2-layer cell factories (NUNC, 1200 cm$^2$) in Ham's F12, 10% v/v FCS and antibiotics. Cells were grown to confluency, the medium removed and the cells were then rinsed 3-times with PBS and re-fed with 200 ml of Ham's F12 without FCS but supplemented with antibiotics and 10 mM-NH$_4$Cl. After 4 days in culture, the medium was collected and replaced with Ham's F12, 10% v/v FCS and PSK but without NH$_4$Cl for 3 days. This cycle was repeated several times. The conditioned serum free Ham's F12 medium supplemented with NH$_4$Cl was collected, clarified by filtration (0.2 μM filture; Millipore) and stored at 4° C.

The rIDS was purified from the collected medium by a 3-step column procedure. The medium was dialysed overnight at 4° C. against 30 mM-Tris/HCl, pH 7.0/10% v/v glycerol/0.1 mM-DTE/3 mM-NaN$_3$ (buffer A) and was applied to a PBE94 column (8 cm×1.5 cm) equilibrated in buffer A (flow-rate 1.0 ml/min) and then washed with 100 ml of buffer A. Bound proteins were diluted with polybuffer 74 that had been diltured 1:18 with water, the pH adjusted to 4.0 with HCl and the solution made 10% v/v in glycerol, 0.1 mM-DTE and 3 mM-NaN$_3$. The column was further eluted with 100 ml 15 mM-ditheriothreitol/3 mM-NaN$_3$ (buffer B). The rIDS eluted in buffer B was applied at a flow-rate of 1.0 ml/mm to a Blue A agarose column (6 cm×0.7 cm) also equilibrated in buffer B. The rIDS activity from this step was applied in 1.0 ml volumes to an LKB Ultrachrom GTi f.p.l.c. system with a TSK (G3000SW Ultrapac column (30 cm×0.8 cm) equilibrated and eluted in buffer B at a flow-rate of 0.5 ml/min and pressure of 150 kPa. Fractions containing rIDS activity were pooled and analysed under denaturing and non-denaturing condition on SDS-PAGE (10% w/v acrylamide) to estimate apparent subunit size. Gels were stained with either Gradipure Colloidal Electrophoresis Gel Stain (Gradipure, Pyrmont, NSW) or silver stained according to the method of Merril et al (32). Native molecular mass was determined using the f.p.l.c. system as described elsewhere (3) Kinetic (Km, Vmax, pH optima) and inhibition data were obtained as previously described (3).

Endoglycosidase F treatment of IDS

To two identical 60 μl samples, each containing 2.5 μg of rIDS, was added an equal volume of buffer containing 100 mM-sodium phosphate, pH 6.1/50 mM-EDTA/1% v/v Nonidet P40/0.1% v/v SDS/1% v/v 2-mercaptoethanol. After boiling both samples for 5 min, to one was added 1 unit and to the other 5 units of endoglycosidase. Both samples were incubated for 17 h at 37° C. A control sample was untreated but stored in similar buffer conditions at 4° C. Bromophenol blue was added to each sample before analysis on SDS-PAGE. Molecular-mass standards were applied to SDS-PAGE in the same buffer as the enzyme samples.

2. RESULTS

Construction of IDS expression vectors

Figure 4:
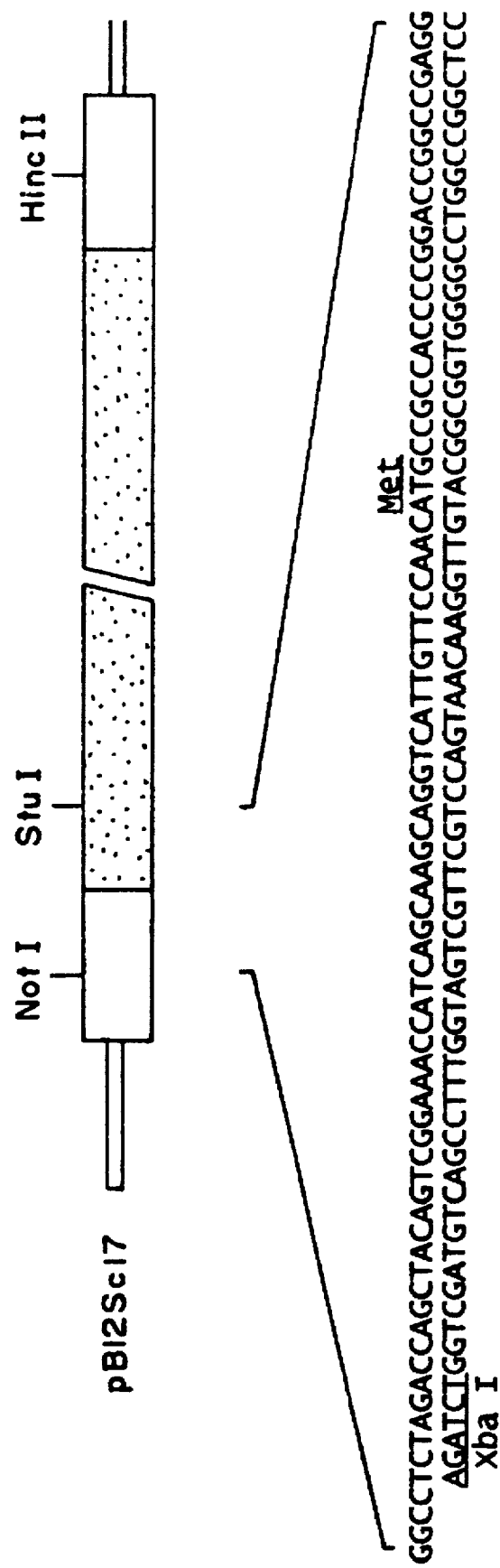
FIG. 4 is a schematic representation showing the construction of a chimeric IDS cDNA. The full length IDS cDNA clone, pB12Sc17, is shown with the unique NotI, StuI and HincII restriction enzyme sites marked. The narrow open bar indicates plasmid vector sequence, the solid bar coding sequence and the large open bar non-coding sequence. The oligonucleotide sequence inserted in place of the sequence removed by NotI/StuI digestion is shown below with the unique XbaI restriction enzyme site and the ATG (Met) initiation codon indicated.

An initial expression construct containing an IDS cDNA from pB12Sc17 cloned into pRSVN.08 expressed I2S at very low levels when introduced into CHO-K1 cells. A chimeric I2S cDNA was then made by replacing the 5' non-coding sequence of the I2S cDNA with 45 bp of the rat preproinsulin leader sequence (FIG. 4) as an analogous chimeric N-acetylgalactosamine-4-sulphatase cDNA construct resulted in the expression of high levels of enzyme activity in the same system (27). Briefly, the sequence shown in FIG. 4 was synthesised as two complementary oligonucleotides which were then kinased and annealed. The resulting double stranded fragment was then cloned between the dephosphorylated NotI and StuI sites of pB12Sc17. The resulting construct was designated pB12SNC.1. The IDS cDNA insert was then excised from pB12SNC.1 with XbaI and HincII and cloned into XbaI/EcoRV restricted and dephosphorylated pRSVN.08 resulting in the construct pRSVN.2SNC1. In order to further increase expression of rIDS the chimeric rIDS cDNA was placed under the transcriptional control of the human elongation factor-1α (EF-1α) gene promoter. This was done by excising the RSV-LTR from pRSVN.2SNC1 by SalI/XbaI digestion and inserting the HindIII/XbaI fragment from pEF-BOS (32), after making the HindIII and SalI ends blunt by filling in with the Klenow fragment of DNA polymerase I. This construct was designated pEFN.2SNC1. Both pRSVN.2SNC1 and pEFN.2SNC1 were electroporated into CHO-K1 cells and G418 resistant clonal cell lines isolated. Individual clones were assayed for secretion of IDS activity into the culture medium. Replacement of RSV-LTR promoter with EF-1α promoter resulted in a 2-fold enhancement of IDS expression. A clonal cell line, CHOEFI2S-9, was selected on the basis of maximum expression of IDS activity. This clone secreted IDS such that after 5 days of culture approximately 11 mg of IDS accumulated per litre of medium.

Large-scale production of rIDS

Conditioned serum-free Ham's F12 medium containing NH$_4$Cl was collected as described above. Enzyme was collected in this manner to facilitate purification by minimising total protein in medium. As prolonged exposure to this medium resulted in loss of cell viability the cells were cycled in Ham's F12 with 10% v/v FCS to allow recovery. A total of 1 litre of serum free medium, containing approximately 11 mg of rIDS was collected in this manner.

Figure 5:
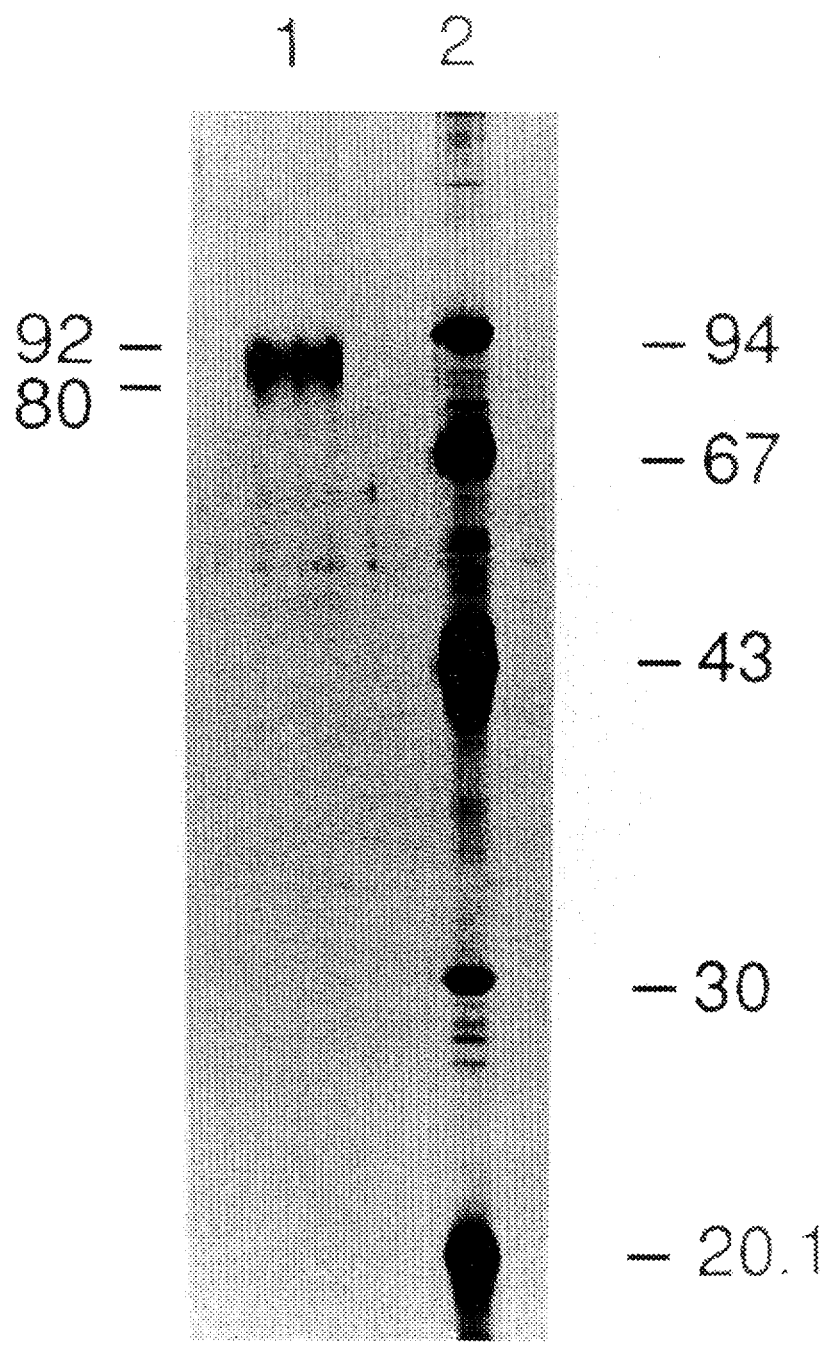
FIG. 5 is a photographic representation of SDS/PAGE of recombinant (r) IDS. rIDS (lane 1) and molecular mass standards (lane 2) were reduced with DTE and electrophoresed as detailed in Example 2 and then Silver stained. The sizes of the molecular mass standards are indicated on the right of the figure and the estimated mass of the rIDS on the left. All massess are in kDa.

The rIDS bound very tightly to PBE94 medium and not not eluted in significant amount during polybuffer elution (less than 10% of the total enzyme recovered from this column was eluted with polybuffer, pool A). The majority of rIDS (pool B) had a pI of <4.0 and required NaCl for elution. Enzyme was eluted in buffer B in concentrated form (essentially in one 10 ml fraction). This permitted direct application to Blue A agarose. Although the rIDS did not bind to this matrix it was a necessary step to remove some minor contaminating proteins which were observed after f.p.l.c. when the enzyme from the chromatofocusing step was applied directly to f.p.l.c. Recovery of activity from Blue A agarose was 80%. The final step in the purification (f.p.l.c.) resulted in overall recovery of greater than 15% activity. The estimated native molecular mass on f.p.l.c. was 90 kDa. A single diffuse protein band of 80–92 kDa was observed when a sample from the f.p.l.c. step was subjected to SDS-PAGE (FIG. 5). This diffuse band was observed on SDS-PAGE run under reducing or non-reducing conditions indicative of a single subunit species with no disulphide bonding. Correlation of the protein species observed as a diffuse band on SDS-PAGE with IDS activity was demonstrated by PAGE run under non-reducing conditions, according to the method of Laemmli (33), but with the modification that SDS was omitted from all buffers. Identical amounts of enzyme were applied to 2 lanes of the gel. One lane was stained for protein and as with SDS-PAGE a single diffuse band was observed. The other was cut into 2 mm slices and each slice was incubated in 4-times the volume of assay mix at 37° C. overnight. When corrected for swelling which occurred during the staining procedure, the position of the diffuse band corresponded to that of IDS activity in the lane that was sliced and assayed.

Figure 6:
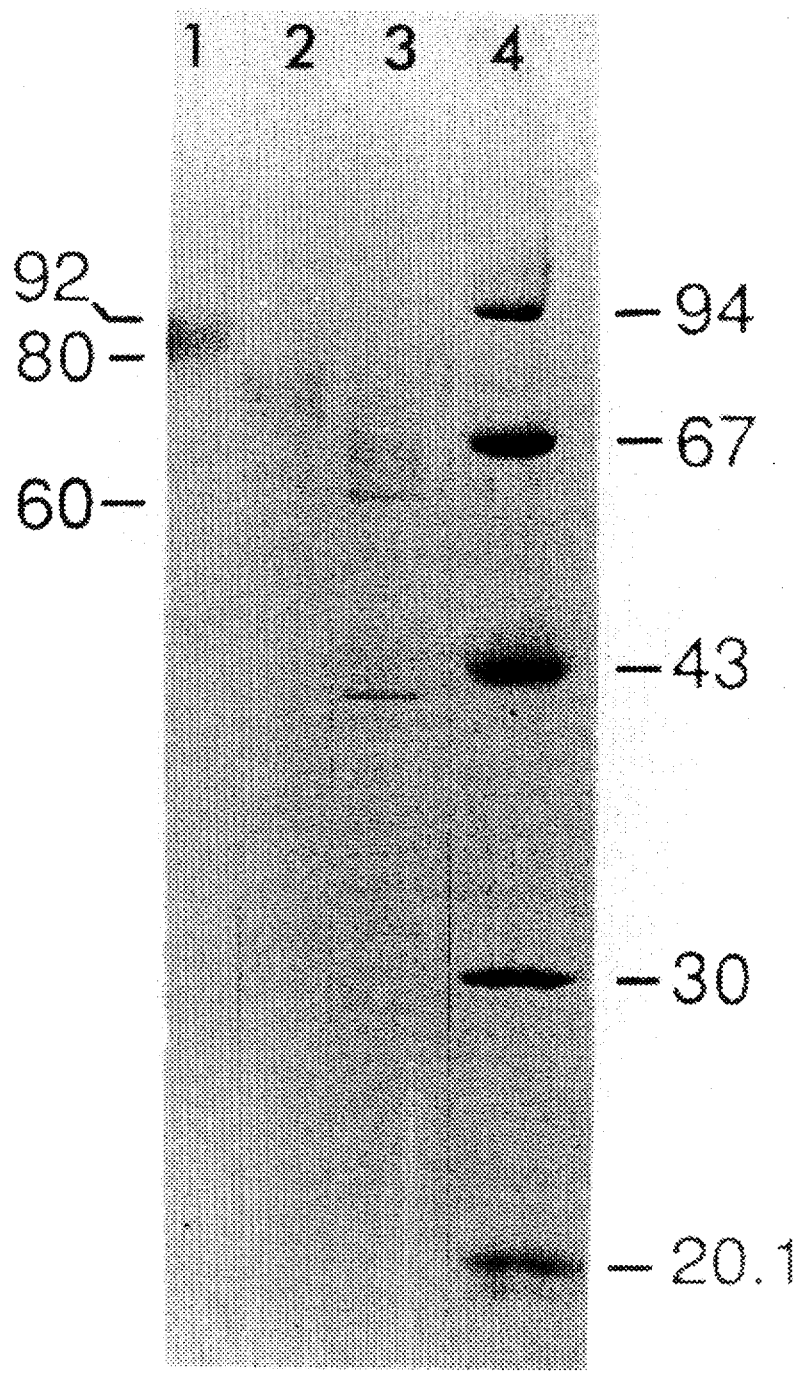
FIG. 6 is a photographic representation showing SDS/PAGE of rIDS after treatment with endoglycosidase F. rIDS was treated with endoglycosidase F, reduced, electrophoresed and stained with Gradipure Colloidal Gel Stain. Lane 1 contains untreated rIDS and lanes 2 and 3 rIDS treated with 1 and 5 units of endoglycosidase F, respectively. Lane 4 contains molecular mass standards with the sizes, in kDa, indicated to the right of the figure.

The molecular size of IDS (after cleavage of the signal peptide) estimated from cDNA sequence data indicated a maximum of 58 kDa with 7 potential glycosylation sites see Example 1). The mature or processed forms of IDS had various molecular sizes depending on the column matrix used. The native molecular size varied from 42 kDa to 65 kDa while, on a denaturing SDS-PAGE, two polypeptide bands of 43 kDa and 14.4 kDa were consistently observed. The recombinant form of IDS had a markedly larger molecular size (80–90 kDa; FIG. 5) than predicted. The diffuse nature of the Coomassie-stained band on SDS-PAGE implied that the protein was highly and variably glycosylated. To test the hypothesis that the difference in the observed Mr and the expected estimated value was due to carbohydrate, rIDS was treated with endoglycosidase F as outlined above. Treatment with 1 unit of endoglycosidase F resulted in a decrease in Mr (70 kDa–80 kDa). However, the enzyme still migrated as a diffuse band on SDS-PAGE (FIG. 6, lane 1). Lane 2, which shows the result of treatment with 5-times the concentration of endoglycosidase F, demonstrates the presence of a tightly staining 60 kDa protein band with a diffuse band above it (62 kDa to 68 kDa). Other bands are due to endoglycosidase F.

These data suggest that the 60 kDa band is the end product of the deglycosylation of rIDS by endoglycosidase F and that the diffuse bands in both lanes are the result of incomplete digestion. Endoglycosidase F cleaves the glycosidic bond between GlcNAc residues of the chitobiose core in the N-linked carbohydrate chains resulting in one GlcNAc residue remaining linked to asparagine. This would account for approximately 1540 kDa clue to carbohydrate if all 7 of the glycosylation sites were utilised and may therefore account for the molecular size of IDS after endoglycosidase F treatment as being 60 kDa rather than 58 kDa.

Kinetics of rIDS

Although both the liver and rIDS show a similar Km towards the disaccharide substrate (IdoA2S-anM6S) in the standard assay (50 mM sodium acetate pH 4.5 and 500 µg/ml BSA) they have a substantially different Vmax. This suggests that the recombinant form of the enzyme may be less efficient in turning over the substrate than the mature form. Alternatively, this may reflect a difference between enzyme produced in CHO cells and in liver. Both the (CHO) recombinant and (liver) mature form of the enzyme have similar pH optima and specific activities (Table 2).

Inhibition studies showed that the rIDS was similar to the liver enzyme with regard to inhibition by sulphate, phosphate and copper ions. The rIDS appears to be less sensitive to salt inhibition than liver enzyme (Table 3).

Demonstration of correction of MPS II fibroblasts

Fibroblasts from patients with MPS II store undegraded HS and DS fragments. This storage is reflected in the accumulation of labelled material when the cells are metabolically labelled with $Na_2{}^{35}SO_4$. Supplementing culture medium with rIDS at $5 \times 10^4$ pmol/min per ml resulted in clearance of this stored product to levels comparable to those seen in control fibroblasts (Table 4) and to levels of IDS activity 40- to 80-fold above normal in SF1779 and SF635 respectively. The activity of a second lysosomal enzyme, β-hexosaminidase, was not affected by endocytosis of IDS (Table 4).

To test whether endocytosis of the rIDS occurs via the mannose-6-phosphate receptor MPS II cells (SF-1779) were cultured in medium supplemented with rIDS at $5 \times 10^4$ and $5 \times 10^3$ pmol/min per ml in the presence or absence of 5 mM mannose-6-phosphate. Inhibition of the uptake of IDS activity by mannose-6-phosphate at both doses of enzyme confirmed that uptake is mediated via the mannose-6-phosphate receptor.

Localisation of endocytosed rIDS

Endocytosed rIDS was instrumental in correcting the lysosomal storage in MPS II skin fibroblasts, as demonstrated by the loss of accumulated $S^{35}$-labelled material. Confirmation of the subcellular localisation of the endocytosed enzyme was demonstrated by fractionating the postnuclear supernatant of corrected and control MPSII skin fibroblasts on Percoll gradients as described above. Analysis of these gradients showed that in the corrected MPS II cells, IDS activity fractionated with the lysosomal enzyme β-hexosaminidase in the dense fraction of the gradient. Control MPS II fibroblasts contained no detectable levels of IDS activity and a similar β-hexosaminidase activity profile.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 2

Comparison of the Catalytic Properties of Recombinant and Liver IDS

| | Km (µM) | Vmax (µmol/min per mg) | Specific Activity (µmol/min per mg) | pH Optimum |
|---|---|---|---|---|
| Liver IDS | 4.0 | 80 | 11.9 | 4.5 |
| rIDS | 3.0 | 3.35 | 20.8 | 4.5 |

TABLE 3

Comparison of the Effect of Various Inhibitors on Recombinant and Liver IDS

| | NaCl (mM) | $Na_2SO_4$ (µM) | $Na_2HPO_4$ (µM) | Cu Acetate (mM) |
|---|---|---|---|---|
| Liver IDS | 40 | 50 | 30 | 15 |
| rIDS | 160 | 115 | 35 | 8 |

Values shown are for 50% inhibition of IDS activity. For details, see Materials and Methods section.

TABLE 4

Correction of the MPS II Defect by Recombinant IDS

|  | IDS (pmol/min per mg) | | β-Hexosaminidase (nmol/min per mg) | | $^{35}$S-cpm/mg Cell Protein | |
|---|---|---|---|---|---|---|
| SF-3409 | 13.5 ± 2.2 | (n = 3) | 83.0 ± 7.8 | (n = 3) | 3138 ± 491 | (n = 3) |
| SF-1779 | n.d. | (n = 3) | 150 ± 10 | (n = 3) | 196927 ± 21247 | (n = 3) |
| SF-1779 + rISD | 562 ± 99 | (n = 3) | 118 ± 11 | (n = 3) | 5136 ± 502 | (n = 3) |
| SF-635 | 1.6 ± 1.5 | (n = 3) | 269 ± 29 | (n = 3) | 233080 ± 66010 | (n = 3) |
| SF-635 + rISD | 1140 ± 50 | (n = 3) | 257 ± 14 | (n = 3) | 9018 ± 1988 | (n = 3) | n = number of experimental repeats;
n.d. = none detected

Normal and MPS II fibroblasts were labelled with $Na_2^{35}SO_4$ and exposed to $5 \times 10^4$ pmol/min per ml of rIDS as described in Materials and Methods. Undialysed cell lysates were analysed for IDS activity, total protein, β-hexosaminidase acitivity and radioactivity.

REFERENCES

1. Neufeld, E. F. & Muenzer, J. (1989) in *The Metabolic Basis of Inherited Disease*, eds. Scriver, C. R., Beaudet, A. L., Sly, W. S. & Valle, D. (McGraw-Hill, New York), pp. 1565–1587.
2. Shapiro, L. J. (1989) in *The Metabolic Basis of Inherited Disease*, eds. Scriver, C. R., Beaudet, A. L., Sly, W. S. & Valle, D. (McGraw-Hill, New York), pp. 1945–1964.
3. Bielicki, J., Freeman, C., Clements, P. R. & Hopwood, J. J. (1990) *Biochem, J.*, 271: 75–86.
4. Matsudaira, P., (1987) *J. Biol. Chem.* 262: 10035–10038.
5. Sanger, R., Nicklen, S., & Coulson, A. R. (1977) *Proc. Natl. Acad. Sci. USA* 74: 5463–5467.
6. Nelson, P. V., Carey, W. F., Morris, C. P., & Pollard, A. C. (1989) *Med. J. Aust.* 151: 126–131.
7. Chomczynski, P. & Sacchi, N. (1987) *Anal. Biochem.* 162: 156–159.
8. Reisner, A. H., & Bucholtz, C. (1987) *Nature (London)* 314: 310.
9. Lipman, D. J., Altschul, S. F. & Kececioglu, J. D. (1989) *Proc. Natl. Acad. Sci. USA* 86: 4412–4415.
10. Masuyama, T., Gojobori, T., Aota, S. & Ikemura, T. (1986) *Nucleic Acids Res.* 14: r151-t197.
11. Kozak, M. (1987) *Nucleic Acids Res.* 15: 8125–8131.
12. von Heijne, G. (1986) *Nucleic Acids Res.* 14: 4683–4690.
13. Hasilik, A. & von Figura, K. (1984) in *Lysosomes in Biology and Pathologyeds.* Dingle, J. T. & Sly, W. S. (Elsevier, Amsterdam) Vol. 7, pp. 3–16.
14. Stein, C., Gieselmann, V., Kreysing, J., Schmidt, B., Pohlmann, R., Waheed, A., Meyer, H. E., O'Brien, J. S. & von Figura, K. (1990) *J. Biol. Chem.* 265: 3374–3381.
15. Peters, C., Schmidt, B., Rommerskirch, W., Rupp, K., Zuhlsdorf, M., Vingron, M., Meyer, H. E., Pohlmann, R. & von Figura K. (1990) *J. Biol. Chem.* 265: 3374–3381.
16. Yen, P. H., Marsh, B., Allen, E., Tsai, S. P., Ellison, J., Connolly, L., Neiswanger, K. & Shapiro, L. J. (1988) *Cell* 55: 1123–1135.
17. Oshima, A., Kyle, J. W., Miller, R. D., Hoffman, J. W., Powell, P., Grubb, J. H., Sly, W. S., Tropak, M., Guise, S. & Gravel, R. A. (1987) *Proc. Natl. Acad. Sci. USA* 84: 685–689.
18. Morreau, H., Galjart, M. J., Gillemands, N., Willemsen, R., van Horst, T. J. & d'Azzo, A. (1989) *J. Biol. Chem.* 264: 20655–20663.
19. Robertson, D. A., Freeman, C., Nelson, P. V., Morris, C. P. & Hopwood, J. J. (1988) *Biochem. Biophys. Res. Commun.* 157: 218–224.
20. Yen, P. H., Allen, E., Marsh, B., Mohandas, T., Wang, N., Taggart, R. T. & Shaapiro, L. J. (1987) *Cell* 49: 443–454.
21. Stein, C., Hille, A., Seidel, J., Rijnbout, S., Waheed, A., Schmidt, B., Geuze, H & von Figura, K. (1989) *J. Biol. Chem.* 254: 13865–13872.
22. Sasaki, H., Yamada, K., Akasaka, K., Kawasaki, H., Suzuki, K., Saito, A., Sato, M. & Shimada, H. (1988) *Eur. J. Biochem.* 177: 9–13.
23. Dayhoff, M. O., Schwartz, R. M. & Orcatt, B. C. (1978) in *Atlas of Protein Sequence and Structure*, ed. Dayhoff, M. O. (Natl. Biomed. Res. Found., Washington, D.C.) Vol. 5, Suppl. 3, pp 345–352.
24. Lee, G. D. & van Etten, R. L. (1975) *Arch. Biochem. Biophys.* 171: 425–434.
25. James, G. T. (1979) *Arch. Biochem. Biophys.* 197: 57–62.
26. Ausubel, F. M., Brent, R., Kingston, R. E., Moore, D. D., Seidman, J. G., Smith, J. A. and Struhl, K. (1989) *Current Protocols in Molecular Biology*, Wiley Interscience, New York.
27. Anson, D. S., Taylor, J. A., Bielicki, J., Harper, G. S., Peters, C., Gibson, G. J. and Hopwood, J. J. (1992) Biochem. J. 284: 789–794.
28. Hopwood, J. J., Muller, V., Harrison, J. R., Carey, W. F., Elliott, H., Robertson, E. F. and Pollard, A. C. (1982) *Med. J. Aust.* 1: 257–260.
29. Lowry, O. H., Rosebrough, N. H. Farr, A. L. and Randell,. R. J. (1951) *J. Biol. Chem.* 193: 265–275.
30. Leaback, D. H. and Walker, P. G. (1961) *Biochem. J.* 78: 151–156.
31. Merril, C. R. Goldman, D., Sedman, S. A. and Ebert, M. H. (1981) *Science* 211: 1437–1438.
32. Mizushima, S. and Nagata, S. (1990) *Nuc. Acids. Res.* 18: 5322.
33. Laemmli, U.K. (1970) *Nature* (London) 227: 680–685.

The claims defining the invention are follows:

1. A method for producing a glycosylated iduronate-2-sulfatase enzyme which comprises culturing a host cell containing a nucleic acid encoding the enzymatically active iduronate-2-sulfatase polypeptide wherein said host cell glycosylates said polypeptide to a greater degree than a native iduronate-2-sulfatase polypeptide expressed by a natural human liver cell.

2. The method of claim 1 wherein said host cell glycosylates said iduronate 2-sulfatase polypeptide such that said polypeptide has a molecular weight as determined by SDS/PAGE of about 5 to about 40 kilodaltons more than said naturally-occurring iduronate 2-sulfatase isolated from human liver cells.

3. The method of claim 1 wherein said glycosylated iduronate 2-sulfatase enzyme has a molecular weight of about 65 kilodaltons to about 95 kilodaltons as determined by SDS/PAGE.

4. The method of claim 1 wherein said host cell is CHO-KI.

5. The method of claim 1 wherein said host cell is CHO-Lec1.

* * * * *

UNITED STATES PATENT AND TRADEMARK OFFICE
CERTIFICATE OF CORRECTION

PATENT NO. : 5,798,239

DATED : August 25, 1998

INVENTOR(S) : Peter J. Wilson, et al.

It is certified that error appears in the above-identified patent and that said Letters Patent are hereby corrected as shown below:

Column 1, line 35: "uriue" should read --urine--

Column 4, line 23: "IOS" should read --IDS--

Column 6, line 41: "1979" should read --1976--

Column 11, line 19: "20" should read --200--

Column 11, line 19, "2" should read --20--

Column 11, line 57: "C" first occurrence should read --G--

Column 11, line 61: "P|" should read --P]--

Column 13, line 37: "MPS-11" should read --MPS-II--

Column 13, line 39: "A" should read -- $\lambda$ --

Column 14, line 27: delete --t--

UNITED STATES PATENT AND TRADEMARK OFFICE
CERTIFICATE OF CORRECTION

PATENT NO. : 5,798,239
DATED : August 25, 1998
INVENTOR(S) : Peter J. Wilson, et al.

It is certified that error appears in the above-identified patent and that said Letters Patent are hereby corrected as shown below:

Column 15, line 30: "EXAMPLE2" should read --EXAMPLE 2--

Column 16, line 12: after "described" insert --in Stanley et al Somat Cell Genet. vol 3(1977) pp 391-405.--

Column 16, line 31: "Hexosamidase" should read --Hexosamidase--

Column 17, line 37: "(G" should read --G--

Column 19, line 37: "clue" should read --due--

Signed and Sealed this

Fourth Day of January, 2000

Attest:

Attesting Officer

*Acting Commissioner of Patents and Trademarks*

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 2297 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 125..1774

( x i ) SEQUENCE DESCRIPTION: SEQ ID NO:1:

```
CGGCTGTGTT GCGCAGTCTT CATGGGTTCC CGACGAGGAG GTCTCTGTGG CTGCGGCGGC         60

TGCTAACTGC GCCACCTGCT GCAGCCTGTC CCCGCCGCTC TGAAGCGGCC GCGTCGAAGC        120

CGAA ATG CCG CCA CCC CGG ACC GGC CGA GGC CTT CTC TGG CTG GGT CTG         169
     Met Pro Pro Pro Arg Thr Gly Arg Gly Leu Leu Trp Leu Gly Leu
       1               5                  10                   15

GTT CTG AGC TCC GTC TGC GTC GCC CTC GGA TCC GAA ACG CAG GCC AAC          217
Val Leu Ser Ser Val Cys Val Ala Leu Gly Ser Glu Thr Gln Ala Asn
                 20                  25                  30

TCG ACC ACA GAT GCT CTG AAC GTT CTT CTC ATC ATC GTG GAT GAC CTG          265
Ser Thr Thr Asp Ala Leu Asn Val Leu Leu Ile Ile Val Asp Asp Leu
             35                  40                  45

CGC CCC TCC CTG GGC TGT TAT GGG GAT AAG CTG GTG AGG TCC CCA AAT          313
Arg Pro Ser Leu Gly Cys Tyr Gly Asp Lys Leu Val Arg Ser Pro Asn
         50                  55                  60

ATT GAC CAA CTG GCA TCC CAC AGC CTC CTC TTC CAG AAT GCC TTT GCG          361
Ile Asp Gln Leu Ala Ser His Ser Leu Leu Phe Gln Asn Ala Phe Ala
     65                  70                  75

CAG CAA GCA GTG TGC GCC CCG AGC CGC GTT TCT TTC CTC ACT GGC AGG          409
Gln Gln Ala Val Cys Ala Pro Ser Arg Val Ser Phe Leu Thr Gly Arg
 80                  85                  90                  95

AGA CCT GAC ACC ACC CGC CTG TAC GAC TTC AAC TCC TAC TGG AGG GTG          457
Arg Pro Asp Thr Thr Arg Leu Tyr Asp Phe Asn Ser Tyr Trp Arg Val
                100                 105                 110

CAC GCT GGA AAC TTC TCC ACC ATC CCC CAG TAC TTC AAG GAG AAT GGC          505
His Ala Gly Asn Phe Ser Thr Ile Pro Gln Tyr Phe Lys Glu Asn Gly
             115                 120                 125

TAT GTG ACC ATG TCG GTG GGA AAA GTC TTT CAC CCT GGG ATA TCT TCT          553
Tyr Val Thr Met Ser Val Gly Lys Val Phe His Pro Gly Ile Ser Ser
         130                 135                 140

AAC CAT ACC GAT GAT TCT CCG TAT AGC TGG TCT TTT CCA CCT TAT CAT          601
Asn His Thr Asp Asp Ser Pro Tyr Ser Trp Ser Phe Pro Pro Tyr His
     145                 150                 155

CCT TCC TCT GAG AAG TAT GAA AAC ACT AAG ACA TGT CGA GGG CCA GAT          649
Pro Ser Ser Glu Lys Tyr Glu Asn Thr Lys Thr Cys Arg Gly Pro Asp
160                 165                 170                 175

GGA GAA CTC CAT GCC AAC CTG CTT TGC CCT GTG GAT GTG CTG GAT GTT          697
Gly Glu Leu His Ala Asn Leu Leu Cys Pro Val Asp Val Leu Asp Val
                180                 185                 190

CCC GAG GGC ACC TTG CCT GAC AAA CAG AGC ACT GAG CAA GCC ATA CAG          745
Pro Glu Gly Thr Leu Pro Asp Lys Gln Ser Thr Glu Gln Ala Ile Gln
            195                 200                 205
```

| | | | | | | | | | | | | | | | | |
|---|---|---|---|---|---|---|---|---|---|---|---|---|---|---|---|---|
| TTG | TTG | GAA | AAG | ATG | AAA | ACG | TCA | GCC | AGT | CCT | TTC | TTC | CTG | GCC | GTT | 793 |
| Leu | Leu | Glu 210 | Lys | Met | Lys | Thr | Ser 215 | Ala | Ser | Pro | Phe | Phe 220 | Leu | Ala | Val | |
| GGG | TAT | CAT | AAG | CCA | CAC | ATC | CCC | TTC | AGA | TAC | CCC | AAG | GAA | TTT | CAG | 841 |
| Gly | Tyr 225 | His | Lys | Pro | His | Ile 230 | Pro | Phe | Arg | Tyr | Pro 235 | Lys | Glu | Phe | Gln | |
| AAG | TTG | TAT | CCC | TTG | GAG | AAC | ATC | ACC | CTG | GCC | CCC | GAT | CCC | GAG | GTC | 889 |
| Lys 240 | Leu | Tyr | Pro | Leu | Glu 245 | Asn | Ile | Thr | Leu | Ala 250 | Pro | Asp | Pro | Glu | Val 255 | |
| CCT | GAT | GGC | CTA | CCC | CCT | GTG | GCC | TAC | AAC | CCC | TGG | ATG | GAC | ATC | AGG | 937 |
| Pro | Asp | Gly | Leu 260 | Pro | Pro | Val | Ala | Tyr 265 | Asn | Pro | Trp | Met | Asp 270 | Ile | Arg | |
| CAA | CGG | GAA | GAC | GTC | CAA | GCC | TTA | AAC | ATC | AGT | GTG | CCG | TAT | GGT | CCA | 985 |
| Gln | Arg | Glu | Asp 275 | Val | Gln | Ala | Leu | Asn 280 | Ile | Ser | Val | Pro | Tyr 285 | Gly | Pro | |
| ATT | CCT | GTG | GAC | TTT | CAG | CGG | AAA | ATC | CGC | CAG | AGC | TAC | TTT | GCC | TCT | 1033 |
| Ile | Pro | Val 290 | Asp | Phe | Gln | Arg | Lys 295 | Ile | Arg | Gln | Ser | Tyr 300 | Phe | Ala | Ser | |
| GTG | TCA | TAT | TTG | GAT | ACA | CAG | GTC | GGC | CGC | CTC | TTG | AGT | GCT | TTG | GAC | 1081 |
| Val | Ser 305 | Tyr | Leu | Asp | Thr | Gln 310 | Val | Gly | Arg | Leu | Leu 315 | Ser | Ala | Leu | Asp | |
| GAT | CTT | CAG | CTG | GCC | AAC | AGC | ACC | ATC | ATT | GCA | TTT | ACC | TCG | GAT | CAT | 1129 |
| Asp 320 | Leu | Gln | Leu | Ala | Asn 325 | Ser | Thr | Ile | Ile | Ala 330 | Phe | Thr | Ser | Asp | His 335 | |
| GGG | TGG | GCT | CTA | GGT | GAA | CAT | GGA | GAA | TGG | GCC | AAA | TAC | AGC | AAT | TTT | 1177 |
| Gly | Trp | Ala | Leu | Gly 340 | Glu | His | Gly | Glu | Trp 345 | Ala | Lys | Tyr | Ser | Asn 350 | Phe | |
| GAT | GTT | GCT | ACC | CAT | GTT | CCC | CTG | ATA | TTC | TAT | GTT | CCT | GGA | AGG | ACG | 1225 |
| Asp | Val | Ala | Thr | His 355 | Val | Pro | Leu | Ile | Phe 360 | Tyr | Val | Pro | Gly | Arg 365 | Thr | |
| GCT | TCA | CTT | CCG | GAG | GCA | GGC | GAG | AAG | CTT | TTC | CCT | TAC | CTC | GAC | CCT | 1273 |
| Ala | Ser | Leu 370 | Pro | Glu | Ala | Gly | Glu 375 | Lys | Leu | Phe | Pro | Tyr 380 | Leu | Asp | Pro | |
| TTT | GAT | TCC | GCC | TCA | CAG | TTG | ATG | GAG | CCA | GGC | AGG | CAA | TCC | ATG | GAC | 1321 |
| Phe | Asp 385 | Ser | Ala | Ser | Gln | Leu 390 | Met | Glu | Pro | Gly | Arg 395 | Gln | Ser | Met | Asp | |
| CTT | GTG | GAA | CTT | GTG | TCT | CTT | TTT | CCC | ACG | CTG | GCT | GGA | CTT | GCA | GGA | 1369 |
| Leu 400 | Val | Glu | Leu | Val | Ser 405 | Leu | Phe | Pro | Thr | Leu 410 | Ala | Gly | Leu | Ala | Gly 415 | |
| CTG | CAG | GTT | CCA | CCT | CGC | TGC | CCC | GTT | CCT | TCA | TTT | CAC | GTT | GAG | CTG | 1417 |
| Leu | Gln | Val | Pro | Pro 420 | Arg | Cys | Pro | Val | Pro 425 | Ser | Phe | His | Val | Glu 430 | Leu | |
| TGC | AGA | GAA | GGC | AAG | AAC | CTT | CTG | AAG | CAT | TTT | CGA | TTC | CGT | GAC | TTG | 1465 |
| Cys | Arg | Glu | Gly 435 | Lys | Asn | Leu | Leu | Lys 440 | His | Phe | Arg | Phe | Arg 445 | Asp | Leu | |
| GAA | GAG | GAT | CCG | TAC | CTC | CCT | GGT | AAT | CCC | CGT | GAA | CTG | ATT | GCC | TAT | 1513 |
| Glu | Glu | Asp | Pro 450 | Tyr | Leu | Pro | Gly | Asn 455 | Pro | Arg | Glu | Leu | Ile 460 | Ala | Tyr | |
| AGC | CAG | TAT | CCC | CGG | CCT | TCA | GAC | ATC | CCT | CAG | TGG | AAT | TCT | GAC | AAG | 1561 |
| Ser | Gln | Tyr 465 | Pro | Arg | Pro | Ser | Asp 470 | Ile | Pro | Gln | Trp | Asn 475 | Ser | Asp | Lys | |
| CCG | AGT | TTA | AAA | GAT | ATA | AAG | ATC | ATG | GGC | TAT | TCC | ATA | CGC | ACC | ATA | 1609 |
| Pro | Ser 480 | Leu | Lys | Asp | Ile | Lys 485 | Ile | Met | Gly | Tyr | Ser 490 | Ile | Arg | Thr | Ile 495 | |
| GAC | TAT | AGG | TAT | ACT | GTG | TGG | GTT | GGC | TTC | AAT | CCT | GAT | GAA | TTT | CTA | 1657 |
| Asp | Tyr | Arg | Tyr | Thr 500 | Val | Trp | Val | Gly | Phe 505 | Asn | Pro | Asp | Glu | Phe 510 | Leu | |
| GCT | AAC | TTT | TCT | GAC | ATC | CAT | GCA | GGG | GAA | CTG | TAT | TTT | GTG | GAT | TCT | 1705 |
| Ala | Asn | Phe | Ser 515 | Asp | Ile | His | Ala | Gly 520 | Glu | Leu | Tyr | Phe | Val 525 | Asp | Ser | |

| | | | | | | | | | | | | | | | | |
|---|---|---|---|---|---|---|---|---|---|---|---|---|---|---|---|---|
| GAC | CCA | TTG | CAG | GAT | CAC | AAT | ATG | TAT | AAT | GAT | TCC | CAA | GGT | GGA | GAT | 1753 |
| Asp | Pro | Leu | Gln | Asp | His | Asn | Met | Tyr | Asn | Asp | Ser | Gln | Gly | Gly | Asp | |
| | | 530 | | | | 535 | | | | | 540 | | | | | |
| CTT | TTC | CAG | TTG | TTG | ATG | CCT | TGAGTTTGC | CAACCATGGA | TGGCAAATGT | | | | | | | 1804 |
| Leu | Phe | Gln | Leu | Leu | Met | Pro | | | | | | | | | | |
| | 545 | | | | | 550 | | | | | | | | | | |

```
GATGTGCTCC  CTTCCAGCTG  GTGAGAGGAG  GAGTTAGAGC  TGGTCGTTTT  GTGATTACCC   1864
ATAATATTGG  AAGCAGCCTG  AGGGCTAGTT  AATCCAAACA  TGCATCAACA  ATTTGGCCTG   1924
AGAATATGTA  ACAGCCAAAC  CTTTTCGTTT  AGTCTTTATT  AAAATTTATA  ATTGGTAATT   1984
GGACCAGTTT  TTTTTTTAAT  TTCCCTCTTT  TTAAAACAGT  TACGGCTTAT  TTACTGAATA   2044
AATACAAAGC  AAACAAACTC  AAGTTATGTC  ATACCTTTGG  ATACGAAGAC  CATACATAAT   2104
AACCAAACAT  AACATTATAC  ACAAAGAATA  CTTTCATTAT  TTGTGGAATT  TAGTGCATTT   2164
CAAAAAGTAA  TCATATATCA  AACTAGGCAC  CACACTAAGT  TCCTGATTAT  TTTGTTTATA   2224
ATTTAATAAT  ATATCTTATG  AGCCCTATAT  ATTCAAAATA  TTATGTTAAC  ATGTAATCCA   2284
TGTTTCTTTT  TCC                                                          2297
```

( 2 ) INFORMATION FOR SEQ ID NO:2:

( i ) SEQUENCE CHARACTERISTICS:
        ( A ) LENGTH: 550 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Pro  Pro  Pro  Arg  Thr  Gly  Arg  Gly  Leu  Leu  Trp  Leu  Gly  Leu  Val
 1              5                        10                       15

Leu  Ser  Ser  Val  Cys  Val  Ala  Leu  Gly  Ser  Glu  Thr  Gln  Ala  Asn  Ser
              20                        25                   30

Thr  Thr  Asp  Ala  Leu  Asn  Val  Leu  Leu  Ile  Ile  Val  Asp  Asp  Leu  Arg
         35                        40                   45

Pro  Ser  Leu  Gly  Cys  Tyr  Gly  Asp  Lys  Leu  Val  Arg  Ser  Pro  Asn  Ile
    50                        55                   60

Asp  Gln  Leu  Ala  Ser  His  Ser  Leu  Leu  Phe  Gln  Asn  Ala  Phe  Ala  Gln
65                        70                   75                        80

Gln  Ala  Val  Cys  Ala  Pro  Ser  Arg  Val  Ser  Phe  Leu  Thr  Gly  Arg  Arg
                        85                   90                        95

Pro  Asp  Thr  Thr  Arg  Leu  Tyr  Asp  Phe  Asn  Ser  Tyr  Trp  Arg  Val  His
              100                       105                      110

Ala  Gly  Asn  Phe  Ser  Thr  Ile  Pro  Gln  Tyr  Phe  Lys  Glu  Asn  Gly  Tyr
              115                       120                      125

Val  Thr  Met  Ser  Val  Gly  Lys  Val  Phe  His  Pro  Gly  Ile  Ser  Ser  Asn
        130                       135                      140

His  Thr  Asp  Asp  Ser  Pro  Tyr  Ser  Trp  Ser  Phe  Pro  Pro  Tyr  His  Pro
145                       150                       155                     160

Ser  Ser  Glu  Lys  Tyr  Glu  Asn  Thr  Lys  Thr  Cys  Arg  Gly  Pro  Asp  Gly
                        165                       170                      175

Glu  Leu  His  Ala  Asn  Leu  Leu  Cys  Pro  Val  Asp  Val  Leu  Asp  Val  Pro
                   180                       185                      190

Glu  Gly  Thr  Leu  Pro  Asp  Lys  Gln  Ser  Thr  Glu  Gln  Ala  Ile  Gln  Leu
              195                       200                      205

Leu  Glu  Lys  Met  Lys  Thr  Ser  Ala  Ser  Pro  Phe  Phe  Leu  Ala  Val  Gly
   210                       215                       220
```

| | | | | | | | | | | | | | | |
|---|---|---|---|---|---|---|---|---|---|---|---|---|---|---|
| Tyr | His | Lys | Pro | His | Ile | Pro | Phe | Arg | Tyr | Pro | Lys | Glu | Phe | Gln | Lys |
| 225 | | | | 230 | | | | | 235 | | | | | 240 |
| Leu | Tyr | Pro | Leu | Glu | Asn | Ile | Thr | Leu | Ala | Pro | Asp | Pro | Glu | Val | Pro |
| | | | | 245 | | | | | 250 | | | | | 255 | |
| Asp | Gly | Leu | Pro | Pro | Val | Ala | Tyr | Asn | Pro | Trp | Met | Asp | Ile | Arg | Gln |
| | | | 260 | | | | | 265 | | | | | 270 | | |
| Arg | Glu | Asp | Val | Gln | Ala | Leu | Asn | Ile | Ser | Val | Pro | Tyr | Gly | Pro | Ile |
| | | 275 | | | | | 280 | | | | | 285 | | | |
| Pro | Val | Asp | Phe | Gln | Arg | Lys | Ile | Arg | Gln | Ser | Tyr | Phe | Ala | Ser | Val |
| | 290 | | | | | 295 | | | | | 300 | | | | |
| Ser | Tyr | Leu | Asp | Thr | Gln | Val | Gly | Arg | Leu | Leu | Ser | Ala | Leu | Asp | Asp |
| 305 | | | | | 310 | | | | | 315 | | | | | 320 |
| Leu | Gln | Leu | Ala | Asn | Ser | Thr | Ile | Ile | Ala | Phe | Thr | Ser | Asp | His | Gly |
| | | | | 325 | | | | | 330 | | | | | 335 | |
| Trp | Ala | Leu | Gly | Glu | His | Gly | Glu | Trp | Ala | Lys | Tyr | Ser | Asn | Phe | Asp |
| | | | 340 | | | | | 345 | | | | | 350 | | |
| Val | Ala | Thr | His | Val | Pro | Leu | Ile | Phe | Tyr | Val | Pro | Gly | Arg | Thr | Ala |
| | | | 355 | | | | 360 | | | | | 365 | | | |
| Ser | Leu | Pro | Glu | Ala | Gly | Glu | Lys | Leu | Phe | Pro | Tyr | Leu | Asp | Pro | Phe |
| | 370 | | | | | 375 | | | | | 380 | | | | |
| Asp | Ser | Ala | Ser | Gln | Leu | Met | Glu | Pro | Gly | Arg | Gln | Ser | Met | Asp | Leu |
| 385 | | | | | 390 | | | | | 395 | | | | | 400 |
| Val | Glu | Leu | Val | Ser | Leu | Phe | Pro | Thr | Leu | Ala | Gly | Leu | Ala | Gly | Leu |
| | | | | 405 | | | | | 410 | | | | | 415 | |
| Gln | Val | Pro | Pro | Arg | Cys | Pro | Val | Pro | Ser | Phe | His | Val | Glu | Leu | Cys |
| | | | 420 | | | | | 425 | | | | | 430 | | |
| Arg | Glu | Gly | Lys | Asn | Leu | Leu | Lys | His | Phe | Arg | Phe | Arg | Asp | Leu | Glu |
| | | 435 | | | | | 440 | | | | | 445 | | | |
| Glu | Asp | Pro | Tyr | Leu | Pro | Gly | Asn | Pro | Arg | Glu | Leu | Ile | Ala | Tyr | Ser |
| | 450 | | | | | 455 | | | | | 460 | | | | |
| Gln | Tyr | Pro | Arg | Pro | Ser | Asp | Ile | Pro | Gln | Trp | Asn | Ser | Asp | Lys | Pro |
| 465 | | | | | 470 | | | | | 475 | | | | | 480 |
| Ser | Leu | Lys | Asp | Ile | Lys | Ile | Met | Gly | Tyr | Ser | Ile | Arg | Thr | Ile | Asp |
| | | | | 485 | | | | | 490 | | | | | 495 | |
| Tyr | Arg | Tyr | Thr | Val | Trp | Val | Gly | Phe | Asn | Pro | Asp | Glu | Phe | Leu | Ala |
| | | | 500 | | | | | 505 | | | | | 510 | | |
| Asn | Phe | Ser | Asp | Ile | His | Ala | Gly | Glu | Leu | Tyr | Phe | Val | Asp | Ser | Asp |
| | | 515 | | | | | 520 | | | | | 525 | | | |
| Pro | Leu | Gln | Asp | His | Asn | Met | Tyr | Asn | Asp | Ser | Gln | Gly | Gly | Asp | Leu |
| | 530 | | | | | 535 | | | | | 540 | | | | |
| Phe | Gln | Leu | Leu | Met | Pro | | | | | | | | | | |
| 545 | | | | | 550 | | | | | | | | | | |

( 2 ) INFORMATION FOR SEQ ID NO:3:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

| | | | | | | | | | | | | | | | |
|---|---|---|---|---|---|---|---|---|---|---|---|---|---|---|---|
| Pro | Arg | Glu | Leu | Ile | Ala | Tyr | Ser | Asn | Tyr | Pro | Arg | Asn | Asn | Ile | Pro |
| 1 | | | | 5 | | | | | 10 | | | | | 15 | |

( 2 ) INFORMATION FOR SEQ ID NO:4:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

```
ACTAGTAGCA   CCTGCTGGAC   GCCGGGAGGG   ACCCGCTGAT   GCTGCTGCA                    49
```

( 2 ) INFORMATION FOR SEQ ID NO:5:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Thr  Ser  Ala  Leu  Asn  Val  Leu  Leu  Ile  Ile  Val  Asp  Asp  Leu  Arg  Pro
1                  5                        10                       15
Ser  Leu  Gly  Asp  Tyr  Asp  Asp  Val  Leu
               20                       25
```

( 2 ) INFORMATION FOR SEQ ID NO:6:

( i ) SEQUENCE CHARACTERISTICS:
        ( A ) LENGTH: 4428 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 332..434

( i x ) FEATURE:
        ( A ) NAME/KEY: intron
        ( B ) LOCATION: 536..537

( i x ) FEATURE:
        ( A ) NAME/KEY: CDS
        ( B ) LOCATION: 693..829

( i x ) FEATURE:
        ( A ) NAME/KEY: intron
        ( B ) LOCATION: 962..963

( i x ) FEATURE:
        ( A ) NAME/KEY: CDS
        ( B ) LOCATION: 1044..1221

( i x ) FEATURE:
        ( A ) NAME/KEY: intron
        ( B ) LOCATION: 1350..1351

( i x ) FEATURE:
        ( A ) NAME/KEY: CDS
        ( B ) LOCATION: 1480..1569

( i x ) FEATURE:
        ( A ) NAME/KEY: intron
        ( B ) LOCATION: 1716..1717

( i x ) FEATURE:
        ( A ) NAME/KEY: CDS
        ( B ) LOCATION: 1841..2041

( i x ) FEATURE:
    ( A ) NAME/KEY: intron
    ( B ) LOCATION: 2206..2207

( i x ) FEATURE:
    ( A ) NAME/KEY: CDS
    ( B ) LOCATION: 2294..2464

( i x ) FEATURE:
    ( A ) NAME/KEY: intron
    ( B ) LOCATION: 2585..2586

( i x ) FEATURE:
    ( A ) NAME/KEY: CDS
    ( B ) LOCATION: 2684..2810

( i x ) FEATURE:
    ( A ) NAME/KEY: intron
    ( B ) LOCATION: 2904..2905

( i x ) FEATURE:
    ( A ) NAME/KEY: CDS
    ( B ) LOCATION: 3033..3206

( i x ) FEATURE:
    ( A ) NAME/KEY: intron
    ( B ) LOCATION: 3308..3309

( i x ) FEATURE:
    ( A ) NAME/KEY: CDS
    ( B ) LOCATION: 3435..3908

( x i ) SEQUENCE DESCRIPTION: SEQ ID NO:6:

```
GCGATCTAGA  CCTAGTTAGC  CAAGTCTCTA  ACGTGACATA  GGGAAAGCTT  GCAATGGCAA      60
CTGGCCGCCC  GTCTGCGCCT  GTCTCTCGCC  ACGCCTATTG  CTGCAGGATG  ACGCGCACCT     120
CTATGAACCC  GCCGTGAGGT  GTGAGTGTGA  CGCAGGGAAG  AGTCGCACGG  ACGCACTCGC     180
GCTGCGGCCA  GCTGCGGGCC  CGGGCGGCGG  CTGTGTTGCG  CAGTCTTCAT  GGGTTCCCGA     240
CGAGGAGGTC  TCTGTGGCTG  CGGCGGCTGC  TAACTGCGCC  ACCTGCTGCA  GCCTGTCCCC     300
GCCGCTCTGA  AGCGGCCGCG  TCGAAGCCGA  AATGCCGCCA  CCCCGGACCG  GCCGAGGCCT     360
TCTCTGGCTG  GGTCTGGTTC  TGAGCTCCGT  CTGCGTCGCC  CTCGGATCCG  AAACGCAGGC     420
CAACTCGACC  ACAGGTGCCG  CCCACGCCCT  CCCTGCCATC  TCTTCTCCCT  TCCTCCCTCC     480
CTTCCTTCCT  CCTTCCTTCT  TTCCTTCCTT  CTTTGTTTAT  ATCCATTCTT  TTTACCCCCC     540
ACTCCCACCC  TTGCTGAGGC  ACAGCGCCCT  CCCTGGCTAG  GCTGTTAGGT  GCAGGGTCCA     600
GCCTTGGGCC  TCTTAGTAAC  CTAGCACCTA  CCATGAGGGA  GGGTTCAGTG  TCAGTGCAGG     660
TTACCTCACC  AAAGCCCCTC  CCTCCTGTGT  AGATGCTCTG  AACGTTCTTC  TCATCATCGT     720
GGATGACCTG  CGCCCCTCCC  TGGGCTGTTA  TGGGGATAAG  CTGGTGAGGT  CCCCAAATAT     780
TGACCAACTG  GCATCCCACA  GCCTCCTCTT  CCAGAATGCC  TTTGCGCAGG  TATGTCTGGG     840
AACCTCTAGC  TGTGGGTGTG  TGCTGCTTCG  TGCACTGAGG  GTTGGGGGCG  GGGAGCTTCA     900
GCTATTGTCA  GATGGCACAG  ATTGTGCGGG  ACATCTTGTT  AGAGGGAAGC  ATAGTCTGGA     960
AAAGGGCGGT  TGCTTGGTTA  CCTAAGAGAT  GGCAGACATG  TTTTGCTGTG  GCGATGCTTA    1020
CCTCTGCTTC  TGCTCCCTAA  CAGCAAGCAG  TGTGCGCCCC  GAGCCGCGTT  TCTTTCCTCA    1080
CTGGCAGGAG  ACCTGACACC  ACCCGCCTGT  ACGACTTCAA  CTCCTACTGG  AGGGTGCACG    1140
CTGGAAACTT  CTCCACCATC  CCCCAGTACT  TCAAGGAGAA  TGGCTATGTG  ACCATGTCGG    1200
TGGGAAAAGT  CTTTCACCCT  GGTACTGCTC  CATGTCCAGA  GTCTGGGTTC  TCTTGGTTTG    1260
TGGTGTCTGA  NTCCAGCATT  CCCATCCTGG  GGATGGGCTG  TCTTTGCAGA  GCCCTCTTCT    1320
GGCTGGGCGA  GTCCCTCGCT  AGTCAGTGCT  TTTGTAGATG  AGGAAACTGA  GCCCCAAAGA    1380
```

| | | | | | |
|---|---|---|---|---|---|
| AGGGAGGNTC | CACTTGCCCA | TTTGTTTACA | GAGTTTTAAT | TATGGGGAGT | GGGGTGTTGA | 1440
| AAGACTCATC | ATGTTTTAAC | AACCTTTTTT | TTTTTCCAAG | GGATATCTTC | TAACCATACC | 1500
| GATGATTCTC | CGTATAGCTG | GTCTTTTCCA | CCTTATCATC | CTTCCTCTGA | GAAGTATGAA | 1560
| AACACTAAGG | TAAGGCTGTG | AAAGGGACAT | TTCTGAAGAG | GAACCACTTT | TTCCTTTGTC | 1620
| ACATAAACTA | CTGGGTATAC | TGCATGTNCT | GTGAAGCTGG | TTATATACCA | CGAAGTTGTG | 1680
| GGTTTCATTT | GTGATAATGT | TTTGACAGAA | GTAAGTTGTT | CAGTCTGAGT | GACTAACACG | 1740
| TGAAGGGCTG | ATTATGTGAA | CATTAAATCT | GTGTGTGTAG | CCTTCATGGC | TTCATNTCTT | 1800
| GCACTTAAAA | AGCTGATGTT | ATATTATTTT | GTTTGAAAG | ACATGTCGAG | GGCCAGATGG | 1860
| AGAACTCCAT | GCCAACCTGC | TTTGCCCTGT | GGATGTGCTG | GATGTTCCCG | AGGGCACCTT | 1920
| GCCTGACAAA | CAGAGCACTG | AGCAAGCCAT | ACAGTTGTTG | GAAAAGATGA | AAACGTCAGC | 1980
| CAGTCCTTTC | TTCCTGGCCG | TTGGGTATCA | TAAGCCACAC | ATCCCCTTCA | GATACCCCAA | 2040
| GGTGAAGAGC | TGGTTGAGGG | CTGATCCAGC | ACAGCTGTGA | CAGCTGTGTT | GTTTGTTGAG | 2100
| GGAGGGATTT | GCACAGGGAA | GGTGGCTACA | TCCTGCCATC | GCCAGGCACC | ATGGTTGCCT | 2160
| GATGGGCACT | AGTGTCCTCA | GTGGAGTAAA | GATGGGATTT | AGAGGTAAAA | GGCAGTATAG | 2220
| ACAGTGATAG | AGCCACAAGC | TTGTGCTTTT | GCTAAAAGAG | TGACAACTTT | GTGGCTTTGT | 2280
| GTTTTTCCCC | AAGGAATTTC | AGAAGTTGTA | TCCCTTGGAG | AACATCACCC | TGGCCCCGA | 2340
| TCCCGAGGTC | CCTGATGGCC | TACCCCCTGT | GGCCTACAAC | CCCTGGATGG | ACATCAGGCA | 2400
| ACGGGAAGAC | GTCCAAGCCT | TAAACATCAG | TGTGCCGTAT | GGTCCAATTC | CTGTGGACTT | 2460
| TCAGGTATCA | AGGACATAGT | TTGGGGATGT | ATTGGACACT | GATGACATAG | TGTCGTAGGT | 2520
| GAAACCACTC | TTCTCAGTAG | ACACAACTCC | ACCTATAATG | TCTTATTAAG | AGCTTTCTTT | 2580
| GTGTGTAGGG | ATTGGAGAG | ATGCACACGG | CAAGCATTAT | CTCTGTATGC | CTTGGCAATT | 2640
| TAAATTGCAG | TCACTCTCAT | TTTTATTTTT | TTTCAATTTG | CAGCGGAAAA | TCCGCCAGAG | 2700
| CTACTTTGCC | TCTGTGTCAT | ATTTGGATAC | ACAGGTCGGC | CGCCTCTTGA | GTGCTTTGGA | 2760
| CGATCTTCAG | CTGGCCAACA | GCACCATCAT | TGCATTTACC | TCGGATCATG | GTAAGCATTT | 2820
| TGAAATTCCC | TGGTGAGTCA | AAACATCTGA | ACTTTCCTGT | GAAACATGCT | TTGCAAAATT | 2880
| GCCATTGACA | TAAACATGGG | TGTGTTTCTT | CTAGGTGATG | AGTTTCTACT | TCCTCTGGTT | 2940
| TTTACAACAG | GAAATGAAAT | GGTATCTAAA | ATAAACAAGC | TGTGGTATGA | TGATTATTCA | 3000
| TTTTCTGTCA | TTCTGTGCTT | TTTATGAACT | AGGGTGGGCT | CTAGGTGAAC | ATGGAGAATG | 3060
| GGCCAAATAC | AGCAATTTTG | ATGTTGCTAC | CCATGTTCCC | CTGATATTCT | ATGTTCCTGG | 3120
| AAGGACGGCT | TCACTTCCGG | AGGCAGGCGA | GAAGCTTTTC | CCTTACCTCG | ACCCTTTTGA | 3180
| TTCCGCCTCA | CAGTTGATGG | AGCCAGGTAT | AAAATATGCT | GAAATGATAT | TGCTTGACAG | 3240
| TAAGATCACC | TTTAGTTTAT | ATGTGAACCA | CTTTATTGAA | TCATAGGCTT | TGGGGTTACA | 3300
| CAGACCCCAA | AGATAAATGG | TGTAAATTAA | AAAAAGAAAA | CATATGGAGC | CCAGACAGGG | 3360
| TCCTTTACTG | CTCCTGCCTG | GCCATGGCAG | GCTTTTATAA | TGTAACCCAT | TCTGCTCTGT | 3420
| CGCTTCCTGT | TTCAGGCAGG | CAATCCATGG | ACCTTGTGGA | ACTTGTGTCT | CTTTTTCCCA | 3480
| CGCTGGCTGG | ACTTGCAGGA | CTGCAGGTTC | CACCTCGCTG | CCCCGTTCCT | TCATTTCACG | 3540
| TTGAGCTGTG | CAGAGAAGGC | AAGAACCTTC | TGAAGCATTT | TCGATTCCGT | GACTTGGAAG | 3600
| AGGATCCGTA | CCTCCCTGGT | AATCCCCGTG | AACTGATTGC | CTATAGCCAG | TATCCCCGGC | 3660
| CTTCAGACAT | CCCTCAGTGG | AATTCTGACA | AGCCGAGTTT | AAAAGATATA | AAGATCATGG | 3720
| GCTATTCCAT | ACGCACCATA | GACTATAGGT | ATACTGTGTG | GGTTGGCTTC | AATCCTGATG | 3780

-continued

| | | | | | |
|---|---|---|---|---|---|
| AATTTCTAGC | TAACTTTTCT | GACATCCATG | CAGGGGAACT | GTATTTTGTG | GATTCTGACC | 3840
| CATTGCAGGA | TCACAATATG | TATAATGATT | CCCAAGGTGG | AGATCTTTTC | CAGTTGTTGA | 3900
| TGCCTTGAGT | TTTGCCAACC | ATGGATGGCA | AATGTGATGT | GCTCCCTTCC | AGCTGGTGAG | 3960
| AGGAGGAGTT | AGAGCTGGTC | GTTTGTGAT | TACCCATAAT | ATTGGAAGCA | GCCTGAGGGC | 4020
| TAGTTAATCC | AAACATGCAT | CAACAATTTG | GCCTGAGAAT | ATGTAACAGC | CAAACCTTTT | 4080
| CGTTTAGTCT | TTATTAAAAT | TTATAATTGG | TAATTGGACC | AGTTTTTTTT | TTAATTTCCC | 4140
| TCTTTTTAAA | ACAGTTACGG | CTTATTTACT | GAATAAATAC | AAAGCAAACA | AACTCAAGTT | 4200
| ATGTCATACC | TTTGGATACG | AAGACCATAC | ATAATAACCA | AACATAACAT | TATACACAAA | 4260
| GAATACTTTC | ATTATTTGTG | GAATTTAGTG | CATTTCAAAA | AGTAATCATA | TATCAAACTA | 4320
| GGCACCACAC | TAAGTTCCTG | ATTATTTTGT | TTATAATTTA | ATAATATATC | TTATGAGCCC | 4380
| TATATATTCA | AAATATTATG | TTAACATGTA | ATCCATGTTT | CTTTTTCC | | 4428

( 2 ) INFORMATION FOR SEQ ID NO:7:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Pro Arg Glu Leu Ile Ala Tyr Ser Xaa Tyr Pro Arg Xaa Xaa Ile Pro
1               5                   10                  15

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Cys Thr Pro Ser Arg
1               5

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

Gly Lys Trp His Leu Gly
1               5

( 2 ) INFORMATION FOR SEQ ID NO:10:

( i ) SEQUENCE CHARACTERISTICS:
        ( A ) LENGTH: 81 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:10:

GGCCTCTAGA CCAGCTACAG TCGGAAACCA TCAGCAAGCA GGTCATTGTT CCAACATGCC    60

GCCACCCCGG ACCGGCCGAG G    81

( 2 ) INFORMATION FOR SEQ ID NO:11:

( i ) SEQUENCE CHARACTERISTICS:
        ( A ) LENGTH: 510 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:11:

```
Thr Arg Arg Pro Asn Val Val Leu Leu Thr Asp Asp Gln Asp Glu
1               5                   10                  15

Val Leu Gly Gly Met Thr Pro Leu Lys Thr Lys Ala Leu Ile Gly
            20                  25                  30

Glu Met Gly Met Thr Phe Ser Ser Ala Tyr Val Pro Ser Ala Leu Cys
            35                  40                  45

Cys Pro Ser Arg Ala Ser Ile Leu Thr Gly Lys Tyr Pro His Asn His
    50                  55                  60

His Val Val Asn Asn Thr Leu Glu Gly Asn Cys Ser Ser Lys Ser Trp
65                  70                  75                  80

Gln Lys Ile Gln Glu Pro Asn Thr Phe Pro Ala Ile Leu Arg Ser Met
                85                  90                  95

Gln Gly Tyr Gln Thr Phe Thr Phe Phe Ala Gly Lys Tyr Leu Asn Glu
                100                 105                 110

Tyr Gly Ala Pro Asp Ala Gly Gly Leu Glu His Val Pro Leu Gly Trp
            115                 120                 125

Ser Tyr Trp Tyr Ala Leu Glu Lys Asn Ser Lys Tyr Tyr Asn Tyr Thr
    130                 135                 140

Leu Ser Ile Asn Gly Lys Ala Arg Lys His Gly Glu Asn Tyr Ser Val
145                 150                 155                 160

Asp Tyr Leu Thr Asp Val Leu Ala Asn Val Ser Leu Asp Phe Leu Asp
                165                 170                 175

Tyr Lys Ser Asn Glu Glu Pro Phe Phe Met Met Ile Ala Thr Pro Ala
            180                 185                 190

Pro His Ser Pro Trp Thr Ala Ala Pro Gln Tyr Gln Lys Ala Phe Gln
        195                 200                 205

Asn Val Phe Ala Pro Arg Asn Lys Asn Phe Asn Ile His Gly Thr Asn
    210                 215                 220

Lys His Trp Leu Ile Arg Gln Ala Lys Thr Pro Met Thr Asn Ser Ser
225                 230                 235                 240

Ile Gln Phe Leu Asp Asn Ala Phe Arg Lys Arg Trp Gln Thr Leu Leu
                245                 250                 255

Ser Val Asp Asp Leu Val Glu Lys Leu Val Lys Arg Leu Glu Phe Thr
            260                 265                 270

Gly Glu Leu Asn Asn Thr Tyr Ile Phe Tyr Thr Ser Asp Asn Gly Tyr
        275                 280                 285

His Thr Gly Gln Phe Ser Leu Pro Ile Asp Lys Arg Gln Leu Tyr Glu
    290                 295                 300

Phe Asp Ile Lys Val Pro Leu Leu Val Arg Gly Pro Gly Ile Lys Pro
305                 310                 315                 320
```

| | | | | | | | | | | | | | | | |
|---|---|---|---|---|---|---|---|---|---|---|---|---|---|---|---|
| Asn | Gln | Thr | Ser | Lys<br>325 | Met | Leu | Val | Ala | Asn<br>330 | Ile | Asp | Leu | Gly | Pro<br>335 | Ile |
| Leu | Asp | Ile | Ala<br>340 | Gly | Tyr | Asp | Leu | Asn<br>345 | Lys | Thr | Gln | Met<br>350 | Asp | Gly | Met |
| Ser | Leu | Leu<br>355 | Pro | Ile | Leu | Arg | Gly<br>360 | Ala | Ser | Asn | Leu | Thr<br>365 | Trp | Arg | Ser |
| Asp | Val<br>370 | Leu | Val | Glu | Tyr | Gln<br>375 | Gly | Glu | Gly | Arg | Asn<br>380 | Val | Thr | Asp | Pro |
| Thr<br>385 | Cys | Pro | Ser | Leu | Ser<br>390 | Pro | Gly | Val | Ser | Gln<br>395 | Cys | Phe | Pro | Asp | Cys<br>400 |
| Val | Cys | Glu | Asp | Ala<br>405 | Tyr | Asn | Asn | Thr | Tyr<br>410 | Ala | Cys | Val | Arg | Thr<br>415 | Met |
| Ser | Ala | Leu | Trp<br>420 | Asn | Leu | Gln | Tyr | Cys<br>425 | Glu | Phe | Asp | Asp | Gln<br>430 | Glu | Val |
| Phe | Val | Glu<br>435 | Val | Tyr | Asn | Leu | Thr<br>440 | Ala | Asp | Pro | Asp | Gln<br>445 | Ile | Thr | Asn |
| Ile | Ala<br>450 | Lys | Thr | Ile | Asp | Pro<br>455 | Glu | Leu | Leu | Gly | Lys<br>460 | Met | Asn | Tyr | Arg |
| Leu<br>465 | Met | Met | Leu | Gln | Ser<br>470 | Cys | Ser | Gly | Pro | Thr<br>475 | Cys | Arg | Thr | Pro | Gly<br>480 |
| Val | Phe | Asp | Pro | Gly<br>485 | Tyr | Arg | Phe | Asp | Pro<br>490 | Arg | Leu | Met | Phe | Ser<br>495 | Asn |
| Arg | Gly | Ser | Val<br>500 | Arg | Thr | Arg | Arg | Phe<br>505 | Ser | Lys | His | Leu | Leu<br>510 | | |

( 2 ) INFORMATION FOR SEQ ID NO:12:

( i ) SEQUENCE CHARACTERISTICS:
      ( A ) LENGTH: 507 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:12:

| | | | | | | | | | | | | | | | |
|---|---|---|---|---|---|---|---|---|---|---|---|---|---|---|---|
| Met<br>1 | Gly | Ala | Pro | Arg<br>5 | Ser | Leu | Leu | Leu | Ala<br>10 | Leu | Ala | Ala | Gly | Leu<br>15 | Ala |
| Val | Ala | Arg | Pro<br>20 | Pro | Asn | Ile | Val | Leu<br>25 | Ile | Phe | Ala | Asp | Asp<br>30 | Leu | Gly |
| Tyr | Gly | Asp | Leu<br>35 | Gly | Cys | Tyr | Gly | His<br>40 | Pro | Ser | Ser | Thr | Thr<br>45 | Pro | Asn |
| Leu | Asp<br>50 | Gln | Leu | Ala | Ala | Gly<br>55 | Gly | Leu | Arg | Phe | Thr<br>60 | Asp | Phe | Tyr | Val |
| Pro<br>65 | Val | Ser | Leu | Gln | Thr<br>70 | Pro | Ser | Arg | Ala | Ala<br>75 | Leu | Leu | Thr | Gln | Arg<br>80 |
| Leu | Pro | Val | Arg | Met<br>85 | Gly | Met | Tyr | Pro | Gly<br>90 | Val | Leu | Val | Pro | Ser<br>95 | Ser |
| Arg | Gly | Gly | Leu<br>100 | Pro | Leu | Glu | Glu | Val<br>105 | Thr | Val | Ala | Glu | Val<br>110 | Leu | Ala |
| Ala | Arg | Gly<br>115 | Tyr | Leu | Thr | Gly | Met<br>120 | Ala | Gly | Lys | Trp | His<br>125 | Leu | Gly | Val |
| Gly | Pro<br>130 | Glu | Gly | Ala | Phe | Leu<br>135 | Pro | Pro | His | Gln | Gly<br>140 | Phe | His | Arg | Phe |
| Leu<br>145 | Gly | Ile | Pro | Tyr | Ser<br>150 | His | Asp | Gln | Gly | Pro<br>155 | Cys | Gln | Asn | Leu | Thr<br>160 |
| Cys | Phe | Pro | Pro | Ala | Thr | Pro | Cys | Asp | Gly | Gly | Cys | Asp | Gln | Gly | Leu |

```
                         165                     170                     175
Val  Pro  Ile  Pro  Leu  Leu  Ala  Asn  Leu  Ser  Val  Glu  Ala  Gln  Pro  Pro
               180                     185                     190

Trp  Leu  Pro  Gly  Leu  Glu  Ala  Arg  Tyr  Met  Ala  Phe  Ala  His  Asp  Leu
               195                     200                     205

Met  Ala  Asp  Ala  Gln  Arg  Gln  Asp  Arg  Pro  Phe  Phe  Leu  Tyr  Tyr  Ala
          210                     215                     220

Ser  His  His  Thr  His  Tyr  Pro  Gln  Phe  Ser  Gly  Gln  Ser  Phe  Ala  Glu
225                           230                     235                     240

Arg  Ser  Gly  Arg  Gly  Pro  Phe  Gly  Asp  Ser  Leu  Met  Glu  Leu  Asp  Ala
                    245                     250                     255

Ala  Val  Gly  Thr  Leu  Met  Thr  Ala  Ile  Gly  Asp  Leu  Gly  Leu  Leu  Glu
               260                     265                     270

Glu  Thr  Leu  Val  Ile  Phe  Thr  Ala  Asp  Asn  Gly  Pro  Glu  Thr  Met  Arg
          275                     280                     285

Met  Ser  Arg  Gly  Gly  Cys  Ser  Gly  Leu  Leu  Arg  Cys  Gly  Lys  Gly  Thr
     290                     295                     300

Thr  Tyr  Glu  Gly  Gly  Val  Arg  Glu  Pro  Ala  Leu  Ala  Phe  Trp  Pro  Gly
305                      310                     315                     320

His  Ile  Ala  Pro  Gly  Val  Thr  His  Glu  Leu  Ala  Ser  Ser  Leu  Asp  Leu
                    325                     330                     335

Leu  Pro  Thr  Leu  Ala  Ala  Leu  Ala  Gly  Ala  Pro  Leu  Pro  Asn  Val  Thr
               340                     345                     350

Leu  Asp  Gly  Phe  Asp  Leu  Arg  Pro  Pro  Ala  Ala  Gly  His  Arg  Gln  Glu
          355                     360                     365

Pro  Ser  Ala  Val  Ser  Leu  Leu  Leu  Pro  Val  Leu  Pro  Arg  Arg  Gly  Pro
     370                     375                     380

Trp  Gly  Phe  Cys  Cys  Ala  Asp  Trp  Lys  Val  Gln  Gly  Ser  Leu  Leu  His
385                      390                     395                     400

Pro  Gly  Ser  Ala  His  Ser  Asp  Thr  Thr  Ala  Asp  Pro  Ala  Cys  His  Ala
                    405                     410                     415

Ser  Ser  Ser  Leu  Thr  Ala  His  Glu  Pro  Pro  Leu  Leu  Tyr  Asp  Leu  Ser
               420                     425                     430

Lys  Asp  Pro  Gly  Glu  Asn  Tyr  Asn  Leu  Leu  Gly  Gly  Val  Ala  Gly  Ala
          435                     440                     445

Thr  Pro  Glu  Val  Leu  Gln  Ala  Leu  Lys  Gln  Leu  Gln  Leu  Leu  Lys  Ala
     450                     455                     460

Gln  Leu  Asp  Ala  Ala  Val  Thr  Phe  Gly  Pro  Ser  Gln  Val  Ala  Arg  Gly
465                      470                     475                     480

Glu  Asp  Pro  Ala  Leu  Gln  Ile  Cys  Cys  His  Pro  Gly  Cys  Thr  Pro  Arg
                    485                     490                     495

Pro  Ala  Cys  Cys  His  Cys  Pro  Asp  Pro  His  Ala
               500                     505
```

( 2 ) INFORMATION FOR SEQ ID NO:13:

( i ) SEQUENCE CHARACTERISTICS:
        ( A ) LENGTH: 533 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:13:

```
Met  Gly  Pro  Arg  Gly  Ala  Ala  Ser  Leu  Pro  Arg  Gly  Pro  Gly  Pro  Arg
1                        5                      10                      15
```

-continued

| | | | | | | | | | | | | | | |
|---|---|---|---|---|---|---|---|---|---|---|---|---|---|---|
|Arg|Leu|Leu|Leu<br>20|Pro|Val|Val|Leu<br>25|Leu|Leu|Leu|Leu<br>30|Leu|Leu| |
|Ala|Pro|Pro<br>35|Gly|Ser|Gly|Ala<br>40|Gly|Ala|Ser|Arg|Pro<br>45|Pro|His|Leu|Val|
|Phe|Leu<br>50|Leu|Ala|Asp|Asp<br>55|Leu|Gly|Trp|Asn<br>60|Asp|Val|Gly|Phe|His|Gly|
|Ser<br>65|Arg|Ile|Arg|Thr|Pro<br>70|His|Leu|Asp|Ala<br>75|Leu|Ala|Ala|Gly|Gly|Val<br>80|
|Leu|Leu|Asp|Asn|Tyr<br>85|Tyr|Thr|Gln|Pro|Leu<br>90|Cys|Thr|Pro|Ser|Arg<br>95|Ser|
|Gln|Leu|Leu|Thr<br>100|Gln|Arg|Tyr|Gln|Ile<br>105|Arg|Thr|Gly|Leu|Gln<br>110|His|Gln|
|Ile|Ile|Trp<br>115|Pro|Cys|Gln|Pro|Ser<br>120|Cys|Val|Pro|Leu|Asp<br>125|Glu|Lys|Leu|
|Leu|Pro<br>130|Gln|Leu|Leu|Lys|Glu<br>135|Ala|Gly|Tyr|Thr|Thr<br>140|His|Met|Val|Gly|
|Lys<br>145|Trp|His|Leu|Gly|Met<br>150|Tyr|Arg|Lys|Glu|Cys<br>155|Leu|Pro|Thr|Arg|Arg<br>160|
|Gly|Phe|Asp|Thr|Tyr<br>165|Phe|Gly|Tyr|Leu|Leu<br>170|Gly|Ser|Glu|Asp|Tyr<br>175|Tyr|
|Ser|His|Glu|Arg<br>180|Cys|Thr|Leu|Ile|Asp<br>185|Ala|Leu|Asn|Val|Thr<br>190|Arg|Cys|
|Ala|Leu|Asp<br>195|Phe|Arg|Asp|Gly|Glu<br>200|Val|Ala|Thr|Gly|Tyr<br>205|Lys|Asn| |
|Met|Tyr<br>210|Ser|Thr|Asn|Ile|Phe<br>215|Thr|Lys|Arg|Ala|Ile<br>220|Ala|Leu|Ile|Thr|
|Asn<br>225|His|Pro|Pro|Glu|Lys<br>230|Pro|Leu|Phe|Leu|Tyr<br>235|Leu|Ala|Leu|Gln|Ser<br>240|
|Val|His|Glu|Pro|Leu<br>245|Gln|Val|Pro|Glu|Glu<br>250|Tyr|Leu|Lys|Pro|Tyr<br>255|Asp|
|Phe|Ile|Gln|Asp<br>260|Lys|Asn|Arg|His|His<br>265|Tyr|Ala|Gly|Met|Val<br>270|Ser|Leu|
|Met|Asp|Glu<br>275|Ala|Val|Gly|Asn|Val<br>280|Thr|Ala|Ala|Leu|Lys<br>285|Ser|Ser|Gly|
|Leu|Trp<br>290|Asn|Asn|Ile|Val|Phe<br>295|Ile|Phe|Ser|Thr|Asp<br>300|Asn|Gly|Gly|Gln|
|Thr<br>305|Leu|Ala|Gly|Gly|Asn<br>310|Asn|Trp|Pro|Leu|Arg<br>315|Gly|Arg|Lys|Trp|Ser<br>320|
|Leu|Trp|Glu|Gly|Gly<br>325|Val|Arg|Gly|Val|Gly<br>330|Phe|Val|Ala|Ser|Pro<br>335|Leu|
|Leu|Lys|Gln|Lys<br>340|Gly|Val|Lys|Asn|Arg<br>345|Glu|Leu|Ile|His|Ile<br>350|Ser|Asp|
|Trp|Leu|Pro<br>355|Thr|Leu|Val|Lys|Leu<br>360|Ala|Arg|Gly|His|Thr<br>365|Asn|Gly|Thr|
|Lys|Pro<br>370|Leu|Asp|Gly|Phe|Asp<br>375|Val|Trp|Lys|Thr|Ile<br>380|Ser|Glu|Gly|Ser|
|Pro<br>385|Ser|Pro|Arg|Ile|Glu<br>390|Leu|Leu|His|Asn|Ile<br>395|Asp|Pro|Asn|Phe|Val<br>400|
|Asp|Ser|Ser|Pro|Cys<br>405|Pro|Arg|Asn|Ser|Met<br>410|Ala|Pro|Ala|Lys|Asp<br>415|Asp|
|Ser|Ser|Leu|Pro<br>420|Glu|Tyr|Ser|Ala|Phe<br>425|Asn|Thr|Ser|Val|His<br>430|Ala|Ala|
|Ile|Arg|His|Gly|Asn|Trp|Lys|Leu|Leu|Thr|Gly|Tyr|Pro|Gly|Cys|Gly|

| | | 435 | | | | 440 | | | | 445 | | | |
|---|---|---|---|---|---|---|---|---|---|---|---|---|---|
| Tyr | Trp | Phe | Pro | Pro | Pro | Ser | Gln | Tyr | Asn | Val | Ser | Glu | Ile | Pro | Ser |
| | 450 | | | | | 455 | | | | 460 | | | |
| Ser | Asp | Pro | Pro | Thr | Lys | Thr | Leu | Trp | Leu | Phe | Asp | Ile | Asp | Arg | Asp |
| 465 | | | | | 470 | | | | 475 | | | | | | 480 |
| Pro | Glu | Glu | Arg | His | Asp | Leu | Ser | Arg | Glu | Tyr | Pro | His | Ile | Val | Thr |
| | | | | 485 | | | | | 490 | | | | | 495 | |
| Lys | Leu | Leu | Ser | Arg | Leu | Gln | Phe | Tyr | His | Lys | His | Ser | Val | Pro | Val |
| | | | 500 | | | | | 505 | | | | | 510 | | |
| Tyr | Phe | Pro | Ala | Gln | Asp | Pro | Arg | Cys | Asp | Pro | Lys | Ala | Thr | Gly | Val |
| | | 515 | | | | | 520 | | | | | 525 | | | |
| Trp | Gly | Pro | Trp | Met | | | | | | | | | | | |
| | 530 | | | | | | | | | | | | | | |

(2) INFORMATION FOR SEQ ID NO:14:

(i) SEQUENCE CHARACTERISTICS:
        (A) LENGTH: 583 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

| Met | Pro | Leu | Arg | Lys | Met | Lys | Ile | Pro | Phe | Leu | Leu | Leu | Phe | Phe | Leu |
|---|---|---|---|---|---|---|---|---|---|---|---|---|---|---|---|
| 1 | | | | 5 | | | | | 10 | | | | | 15 | |
| Trp | Glu | Ala | Glu | Ser | His | Ala | Ala | Ser | Arg | Pro | Asn | Ile | Ile | Leu | Val |
| | | | 20 | | | | | 25 | | | | | 30 | | |
| Met | Ala | Asp | Asp | Leu | Gly | Ile | Gly | Asp | Pro | Gly | Cys | Tyr | Gly | Asn | Lys |
| | | | 35 | | | | 40 | | | | | 45 | | | |
| Thr | Ile | Arg | Thr | Pro | Asn | Ile | Asp | Arg | Leu | Ala | Ser | Gly | Gly | Val | Lys |
| | | 50 | | | | 55 | | | | | 60 | | | | |
| Leu | Thr | Gln | His | Leu | Ala | Ala | Ser | Pro | Leu | Cys | Ile | Pro | Ser | Arg | Ala |
| 65 | | | | | 70 | | | | | 75 | | | | | 80 |
| Ala | Phe | Met | Thr | Gly | Arg | Tyr | Pro | Val | Arg | Ser | Gly | Met | Ala | Ser | Trp |
| | | | | 85 | | | | | 90 | | | | | 95 | |
| Ser | Arg | Thr | Gly | Val | Phe | Leu | Phe | Thr | Ala | Ser | Ser | Gly | Gly | Leu | Pro |
| | | | 100 | | | | | 105 | | | | | 110 | | |
| Thr | Asp | Glu | Ile | Thr | Phe | Ala | Lys | Leu | Leu | Lys | Asp | Gln | Gly | Tyr | Ser |
| | | 115 | | | | | 120 | | | | | 125 | | | |
| Thr | Ala | Leu | Ile | Gly | Lys | Trp | His | Leu | Gly | Met | Ser | Cys | His | Ser | Lys |
| | 130 | | | | | 135 | | | | | 140 | | | | |
| Thr | Asp | Phe | Cys | His | His | Pro | Leu | His | His | Gly | Phe | Asn | Tyr | Phe | Tyr |
| 145 | | | | | 150 | | | | | 155 | | | | | 160 |
| Gly | Ile | Ser | Leu | Thr | Asn | Leu | Arg | Asp | Cys | Lys | Pro | Gly | Glu | Gly | Ser |
| | | | | 165 | | | | 170 | | | | | 175 | | |
| Val | Phe | Thr | Thr | Gly | Phe | Lys | Arg | Leu | Val | Phe | Leu | Pro | Leu | Gln | Ile |
| | | | 180 | | | | | 185 | | | | | 190 | | |
| Val | Gly | Val | Thr | Leu | Leu | Thr | Leu | Ala | Ala | Leu | Asn | Cys | Leu | Gly | Leu |
| | | 195 | | | | | 200 | | | | | 205 | | | |
| Leu | His | Val | Pro | Leu | Gly | Val | Phe | Phe | Ser | Leu | Leu | Phe | Leu | Ala | Ala |
| | 210 | | | | | 215 | | | | | 220 | | | | |
| Leu | Ile | Leu | Thr | Leu | Phe | Leu | Gly | Phe | Leu | His | Tyr | Phe | Arg | Pro | Leu |
| 225 | | | | | 230 | | | | | 235 | | | | | 240 |
| Asn | Cys | Phe | Met | Met | Arg | Asn | Tyr | Glu | Ile | Ile | Gln | Gln | Pro | Met | Ser |
| | | | | 245 | | | | | 250 | | | | | 255 | |

```
Tyr  Asp  Asn  Leu  Thr  Gln  Arg  Leu  Thr  Val  Glu  Ala  Ala  Gln  Phe  Ile
               260                 265                           270

Gln  Arg  Asn  Thr  Glu  Thr  Pro  Phe  Leu  Leu  Val  Leu  Ser  Tyr  Leu  His
          275                      280                      285

Val  His  Thr  Ala  Leu  Phe  Ser  Ser  Lys  Asp  Phe  Ala  Gly  Lys  Ser  Gln
     290                      295                 300

His  Gly  Val  Tyr  Gly  Asp  Ala  Val  Glu  Glu  Met  Asp  Trp  Ser  Val  Gly
305                      310                 315                           320

Gln  Ile  Leu  Asn  Leu  Leu  Asp  Glu  Leu  Arg  Leu  Ala  Asn  Asp  Ile  Leu
                    325                      330                      335

Ile  Tyr  Phe  Thr  Ser  Asp  Gln  Gly  Ala  His  Val  Glu  Glu  Val  Ser  Ser
               340                      345                 350

Lys  Gly  Glu  Ile  His  Gly  Gly  Ser  Asn  Gly  Ile  Tyr  Lys  Gly  Gly  Lys
          355                      360                      365

Ala  Asn  Asn  Trp  Glu  Gly  Gly  Ile  Arg  Val  Pro  Gly  Ile  Leu  Arg  Trp
     370                      375                 380

Pro  Arg  Val  Ile  Gln  Ala  Gly  Gln  Lys  Ile  Asp  Glu  Pro  Thr  Ser  Asn
385                      390                 395                           400

Met  Asp  Ile  Phe  Pro  Thr  Val  Ala  Lys  Leu  Ala  Gly  Ala  Pro  Leu  Pro
               405                      410                      415

Glu  Asp  Arg  Ile  Ile  Asp  Gly  Arg  Asp  Leu  Met  Pro  Leu  Leu  Glu  Gly
               420                      425                 430

Lys  Ser  Gln  Arg  Ser  Asp  His  Glu  Phe  Leu  Phe  His  Tyr  Cys  Asn  Ala
          435                      440                 445

Tyr  Leu  Asn  Ala  Val  Arg  Trp  His  Pro  Gln  Asn  Ser  Thr  Ser  Ile  Trp
     450                      455                 460

Lys  Ala  Phe  Phe  Phe  Thr  Pro  Asn  Phe  Asn  Pro  Val  Gly  Ser  Asn  Gly
465                      470                 475                           480

Cys  Phe  Ala  Thr  His  Val  Cys  Phe  Cys  Phe  Gly  Ser  Tyr  Val  Thr  His
               485                      490                      495

His  Asp  Pro  Pro  Leu  Leu  Phe  Asp  Ile  Ser  Lys  Asp  Pro  Arg  Glu  Arg
               500                      505                 510

Asn  Pro  Leu  Thr  Pro  Ala  Ser  Glu  Pro  Arg  Phe  Tyr  Glu  Ile  Leu  Lys
          515                      520                 525

Val  Met  Gln  Glu  Ala  Ala  Asp  Arg  His  Thr  Gln  Thr  Leu  Pro  Glu  Val
     530                      535                 540

Pro  Asp  Gln  Phe  Ser  Trp  Asn  Asn  Phe  Leu  Trp  Lys  Pro  Trp  Leu  Gln
545                      550                 555                           560

Leu  Cys  Cys  Pro  Ser  Thr  Gly  Leu  Ser  Cys  Gln  Cys  Asp  Arg  Glu  Lys
               565                      570                 575

Gln  Asp  Lys  Arg  Leu  Ser  Arg
               580
```

( 2 ) INFORMATION FOR SEQ ID NO:15:

( i ) SEQUENCE CHARACTERISTICS:
        ( A ) LENGTH: 551 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:15:

```
Met  Lys  Ser  Ala  Pro  Phe  Leu  Phe  Leu  Leu  Gly  Leu  Leu  Gly  Leu  Val
1              5                        10                      15
```

-continued

| | | | | | | | | | | | | | |
|---|---|---|---|---|---|---|---|---|---|---|---|---|---|
|Thr|Ala|Gln|Thr 20|Gln|Asp|Pro|Ala|Leu 25|Leu|Asp|Leu|Leu|Arg 30|Glu|Asn|
|Pro|Asp|Leu 35|Leu|Ser|Leu|Leu|Gln 40|Ser|Asn|Glu|His 45|Arg|Ala|Pro|
|Leu|Val 50|Lys|Pro|Asn|Val 55|Val|Leu|Leu|Val|Ala 60|Asp|Asp|Met|Gly|Ser|
|Gly 65|Asp|Leu|Thr|Ser|Tyr 70|Gly|His|Pro|Thr 75|Gln|Glu|Ala|Gly|Phe|Ile 80|
|Asp|Lys|Met|Ala|Ala 85|Glu|Gly|Leu|Arg|Phe 90|Thr|Asn|Gly|Tyr|Val 95|Gly|
|Asp|Ala|Val|Cys 100|Thr|Pro|Ser|Arg|Ser 105|Ala|Ile|Met|Ile|Gly 110|Arg|Leu|
|Pro|Val|Arg 115|Ile|Gly|Thr|Phe|Gly 120|Glu|Thr|Arg|Val|Phe 125|Leu|Pro|Trp|
|Thr|Lys 130|Thr|Gly|Leu|Pro|Lys 135|Ser|Glu|Leu|Thr|Ile 140|Ala|Glu|Ala|Met|
|Lys 145|Glu|Ala|Gly|Tyr|Ala 150|Ile|Gly|Met|Val|Gly 155|Lys|Trp|His|Leu|Gly 160|
|Met|Asn|Glu|Asn|Ser 165|Ser|Ile|Asp|Gly|Ala 170|His|Leu|Pro|Phe|Asn 175|His|
|Gly|Phe|Asp|Phe 180|Val|Gly|His|Asn|Leu 185|Pro|Phe|Thr|Asn|Ser 190|Trp|Ser|
|Cys|Asp|Asp 195|Thr|Gly|Leu|His|Lys 200|Asp|Phe|Pro|Asp|Ser 205|Gln|Arg|Cys|
|Tyr|Leu 210|Tyr|Val|Asn|Ala|Thr 215|Leu|Val|Ser|Gln|Pro 220|Tyr|Gln|His|Lys|
|Gly 225|Leu|Thr|Gln|Leu|Phe 230|Thr|Asp|Asp|Ala|Leu 235|Gly|Phe|Ile|Glu|Asp 240|
|Asn|His|Ala|Asp|Pro 245|Phe|Phe|Leu|Tyr|Val 250|Ala|Phe|Ala|His|Met 255|His|
|Thr|Ser|Leu|Phe 260|Ser|Ser|Asp|Asp|Phe 265|Ser|Cys|Thr|Ser|Arg 270|Arg|Gly|
|Arg|Tyr|Gly 275|Asp|Asn|Leu|Leu|Glu 280|Met|His|Asp|Ala|Val 285|Asp|Lys|Ile|
|Val|Asp 290|Lys|Leu|Glu|Glu|Asn 295|Asn|Ile|Ser|Glu|Asn 300|Ile|Ile|Ile|Phe|
|Phe 305|Ile|Ser|Asp|His|Gly 310|Pro|His|Arg|Glu|Tyr 315|Cys|Glu|Glu|Gly|Gly 320|
|Asp|Ala|Ser|Ile|Phe 325|Arg|Gly|Gly|Lys|Ser 330|His|Ser|Trp|Glu|Gly 335|Gly|
|His|Arg|Ile|Pro 340|Tyr|Ile|Val|Tyr|Trp 345|Pro|Gly|Thr|Ile|Ser 350|Pro|Gly|
|Ile|Ser|Asn 355|Glu|Ile|Val|Thr|Ser 360|Met|Asp|Ile|Ile|Ala 365|Ile|Ala|Ala|
|Asp|Leu 370|Gly|Gly|Thr|Thr|Leu 375|Pro|Thr|Asp|Arg|Ile 380|Tyr|Asp|Gly|Lys|
|Ser 385|Ile|Lys|Asp|Val|Leu 390|Leu|Glu|Gly|Ser|Ala 395|Ser|Pro|His|Ser|Ser 400|
|Phe|Phe|Tyr|Tyr|Cys 405|Lys|Asp|Asn|Leu|Met 410|Ala|Val|Arg|Val|Gly 415|Lys|
|Tyr|Lys|Ala|His|Phe 420|Arg|Thr|Gln|Arg|Val 425|Arg|Ser|Gln|Asp|Glu 430|Tyr|
|Gly|Leu|Glu|Cys 435|Ala|Gly|Gly|Phe|Pro 440|Leu|Glu|Asp|Tyr|Phe 445|Asp|Cys|

| | | | | | | | | | | | | | | |
|---|---|---|---|---|---|---|---|---|---|---|---|---|---|---|
| Asn | Asp 450 | Cys | Glu | Gly | Asp | Cys 455 | Val | Thr | Glu | His | Asp 460 | Pro | Pro | Leu | Leu |
| Phe 465 | Asp | Leu | Met | Arg | Asp 470 | Pro | Gly | Glu | Ala | Tyr 475 | Pro | Leu | Glu | Ala | Cys 480 |
| Gly | His | Glu | Asp | Val 485 | Phe | Leu | Thr | Val | Lys 490 | Ser | Thr | Val | Glu | Glu 495 | His |
| Lys | Ala | Ala | Leu 500 | Val | Lys | Cys | Thr | Pro 505 | Leu | Leu | Asp | Ser | Phe 510 | Asp | His |
| Ser | Ile | Val 515 | Pro | Cys | Cys | Asn | Pro 520 | Ala | Asn | Cys | Cys | Ile 525 | Cys | Asn | Tyr |
| Val | His 530 | Glu | Pro | Gly | Met | Pro 535 | Glu | Cys | Tyr | Gln | Asp 540 | Gln | Val | Ala | Thr |
| Ala 545 | Ala | Arg | His | Tyr | Arg 550 | Pro | | | | | | | | | |